United States Patent
Mittelman et al.

(10) Patent No.: US 11,242,341 B2
(45) Date of Patent: Feb. 8, 2022

(54) SOLID STATE FORMS OF VALBENAZINE

(71) Applicant: ASSIA CHEMICAL INDUSTRIES LTD., Petach Tikva (IL)

(72) Inventors: Ariel Mittelman, Elad (IL); Sharona Shachan-Tov, Kfar Saba (IL); Abed Masarwa, Tayibe (IL); Rotem Sella-Erez, Tel Aviv (IL); Jonathan Enav, Bnei Brak (IL); Motti Erlich, Petach Tikva (IL); Victoria Machtey, Ariel (IL); Maytal Piran, Rishon LeZion (IL); Marina Yarovoy, Rosh Haayin (IL); Sagit Azran, Givat Shmuel (IL); Einat Kisin-Finfer, Hod Hasharon (IL); Tamar Nidam, Yehud (IL)

(73) Assignee: ASSIA CHEMICAL INDUSTRIES LTD., Petach-Tikva (IL)

( * ) Notice: Subject to any disclaimer, the term of this patent is extended or adjusted under 35 U.S.C. 154(b) by 0 days.

(21) Appl. No.: 16/339,778

(22) PCT Filed: Oct. 6, 2017

(86) PCT No.: PCT/US2017/055561
§ 371 (c)(1),
(2) Date: Apr. 5, 2019

(87) PCT Pub. No.: WO2018/067945
PCT Pub. Date: Apr. 12, 2018

(65) Prior Publication Data
US 2020/0048244 A1    Feb. 13, 2020

Related U.S. Application Data

(60) Provisional application No. 62/404,988, filed on Oct. 6, 2016, provisional application No. 62/406,173, filed on Oct. 10, 2016, provisional application No. 62/407,771, filed on Oct. 13, 2016, provisional application No. 62/424,216, filed on Nov. 18, 2016, provisional application No. 62/462,156, filed on Feb. 22, 2017, provisional application No. 62/530,524, filed on Jul. 10, 2017.

(30) Foreign Application Priority Data

Oct. 6, 2017    (WO) .............. PCT/US2017/055561

(51) Int. Cl.
| | | |
|---|---|---|
| C07D 455/06 | (2006.01) | |
| C07C 53/126 | (2006.01) | |
| C07C 57/15 | (2006.01) | |
| C07C 309/04 | (2006.01) | |
| C07C 309/30 | (2006.01) | |

(52) U.S. Cl.
CPC .......... *C07D 455/06* (2013.01); *C07C 53/126* (2013.01); *C07C 57/15* (2013.01); *C07C 309/04* (2013.01); *C07C 309/30* (2013.01); *C07B 2200/07* (2013.01); *C07B 2200/13* (2013.01)

(58) Field of Classification Search
CPC .... C07D 471/04; A61K 31/4375; A61P 25/00
USPC .......................................................... 546/289
See application file for complete search history.

(56) References Cited

U.S. PATENT DOCUMENTS

| | | | |
|---|---|---|---|
| 8,039,627 B2 | 10/2011 | Gano | |
| 8,039,637 B2 * | 10/2011 | DeMattei | .............. C07C 229/60 548/304.4 |

FOREIGN PATENT DOCUMENTS

| | | |
|---|---|---|
| RU | 2126386 C1 | 2/1999 |
| SU | 1364238 A3 | 12/1987 |
| WO | 2008058261 A1 | 5/2008 |
| WO | 2012000308 A1 | 1/2012 |
| WO | WO-2012000308 A1 * | 1/2012 ............. C07B 57/00 |
| WO | 2017075340 A1 | 5/2017 |
| WO | 2017112857 A1 | 6/2017 |

OTHER PUBLICATIONS

Boldt Karl et al. . Synthesis of (ⱷ )- and ()-Tetrabenazine from the Resolution of a-Dihydrotetrabenazine (Year: 2009).*
Enantiomer Separation: Fundamental and Practical Methods., edited by Fumio Toda, pp. 96, 97 by Faigl and Kozma , (Year: 2004).*
Zhangyu et al , Oreparature and evaluation of tetrabenazine enantiomers and all eight sterioisomers of dihydrotetrabenazine as VMAT2 inhibitors. (Year: 2011).*
Yu Q-S et al: "Preparation and characterization of tetrabenazine entantiomers against vesicular monoamine transporter 2", ACS Medicinal Chemistry Letters, American Chemical Society, US, vol. 1, No. 3, Jun. 10, 2010, pp. 105-109.
Karl G. Boldt et al: "Synthesis of (+)- and (−)-Tetrabenazine from the Resolution of [alpha]-Dihydrotetrabenazine", Synthetic Communications, vol. 39, No. 20, Sep. 18, 2009, pp. 3574-3585.
European Communication issued in corresponding Appl. No. EP 17787796.6 dated Apr. 23, 2020 (11 pages).
Singhal, D. et al., "Drug polymorphism and dosage form design: a practical perspective", Advanced Drug Delivery Reviews, 2004, vol. 56, pp. 335-347.
Balbach, S. et al., 'Pharmaceutical evaluation of early development candidates "The 100 mg approach"', International Journal of Pharmaceutics, 2004, vol. 275, pp. 1-12.

(Continued)

*Primary Examiner* — Rita J Desai
(74) *Attorney, Agent, or Firm* — Carter, Deluca & Farrell LLP

(57) ABSTRACT

Solid state forms of Valbenazine, Valbenazine salts, processes for preparation thereof and pharmaceutical compositions thereof are disclosed. Processes for the preparation of Valbenazine and intermediates in the preparation thereof are further described.

16 Claims, 27 Drawing Sheets

(56) References Cited

OTHER PUBLICATIONS

Examination report No. 1 for standard patent application issued in corresponding Appl. No. 2017340915 dated Mar. 3, 2021 (6 pages).
Second Office Action issued in corresponding Russian application, RU 2019110048, together with Engish language translation and Search report dated Jun. 4, 2021 (25 pages).
Mino R. Caira, "Crystalline Polymorphism of Organic Compounds", Topics in Current Chemistry, vol. 198, pp. 163-208 (1998).
Abu T.M. Serajuddin, "Salt formation to improve drug solubility", Advanced Drug Delivery Reviews, vol. 59, pp. 603-616 (2007).
Yao, et al., "Preparation and evaluation of tetrabenazine enantiomers and all eight stereoisomers of dihydrotetrabenazine as VMAT2 inhibitors", European Journal of Medicinal Chemistry, vol. 46, pp. 1841-1848 (2011).
ISR issued in corresponding Int'l Appl. No. PCT/2017/055561 dated Jan. 19, 2018 (8 pages).

\* cited by examiner

Figure 1: An X-ray powder diffractogram (XRPD) of form L1 of Valbenazine
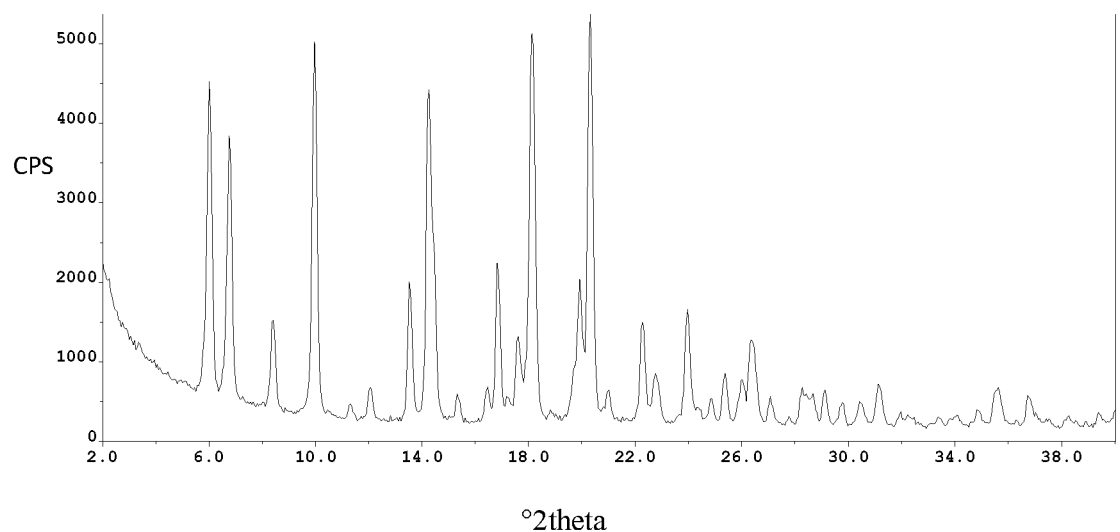

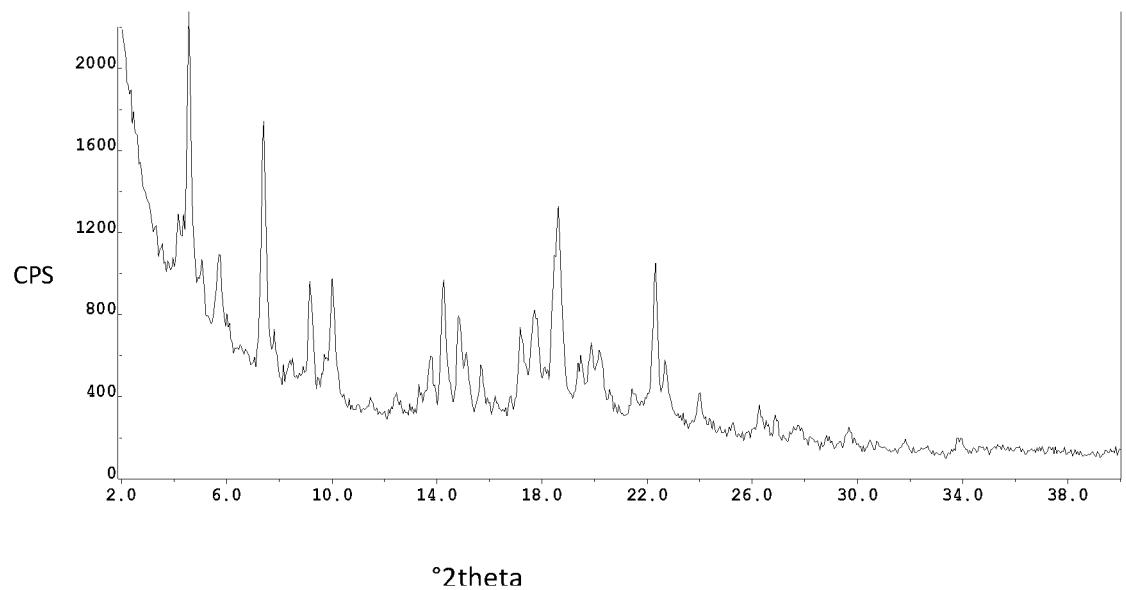
Figure 2: An X-ray powder diffractogram (XRPD) of form L2 of Valbenazine Figure 3: An X-ray powder diffractogram (XRPD) of form L3 of Valbenazine
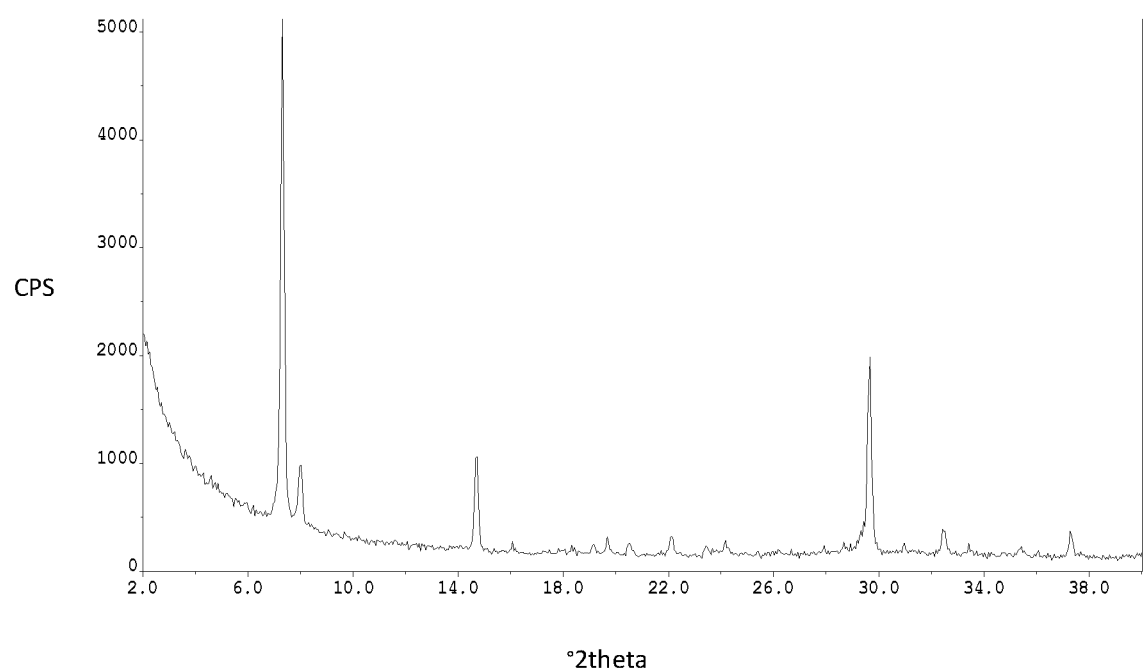

Figure 4: An X-ray powder diffractogram (XRPD) of form L4 of Valbenazine
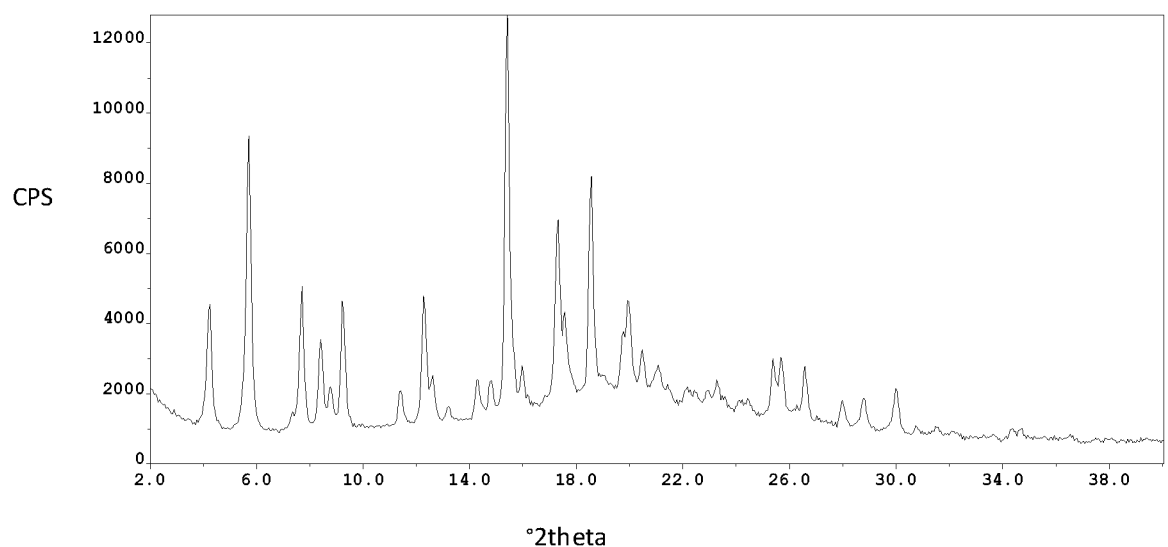

Figure 5: An X-ray powder diffractogram (XRPD) of form L2 of Valbenazine
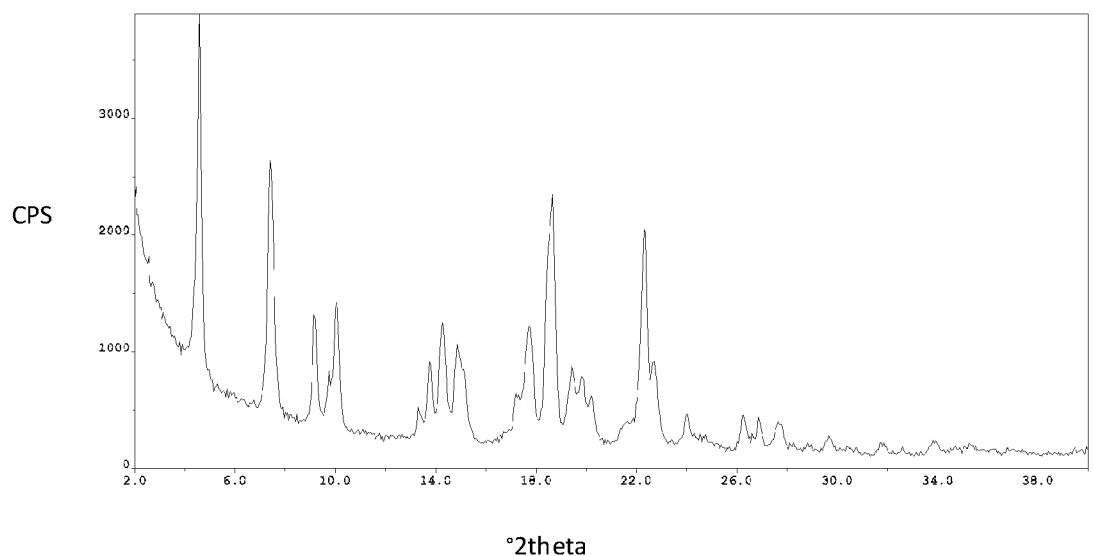

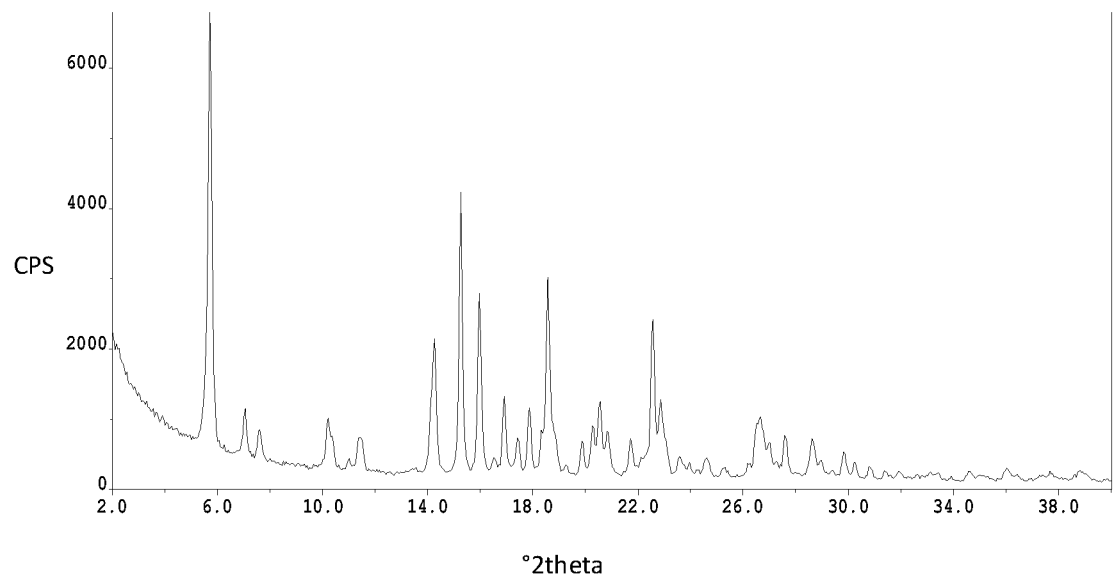
Figure 6: An X-ray powder diffractogram (XRPD) of form T1 of Valbenazine tosylate Figure 7: An X-ray powder diffractogram (XRPD) of form T2 of Valbenazine tosylate
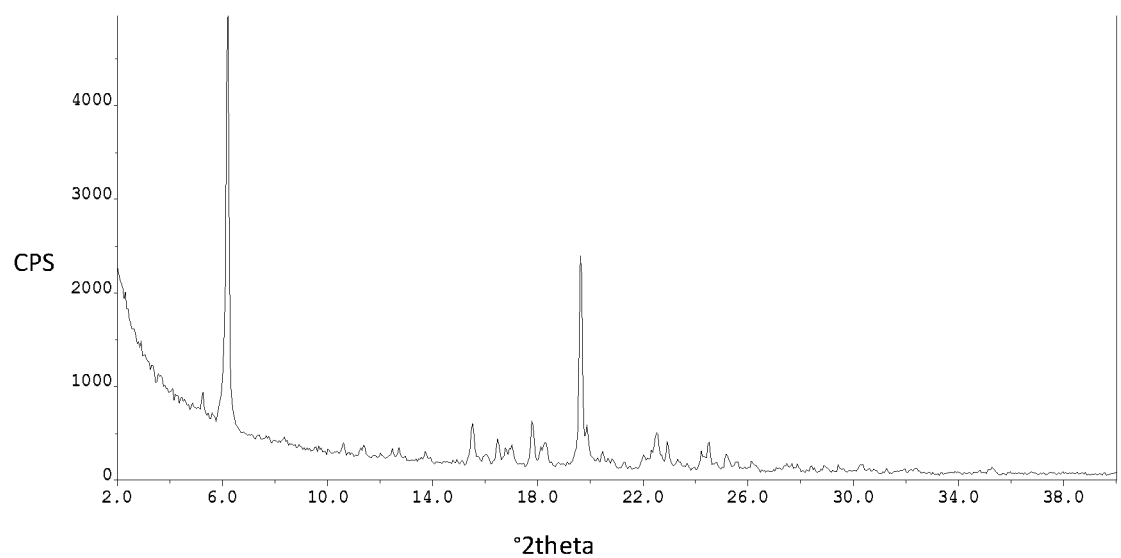

Figure 8: An X-ray powder diffractogram (XRPD) of form T3 of Valbenazine tosylate
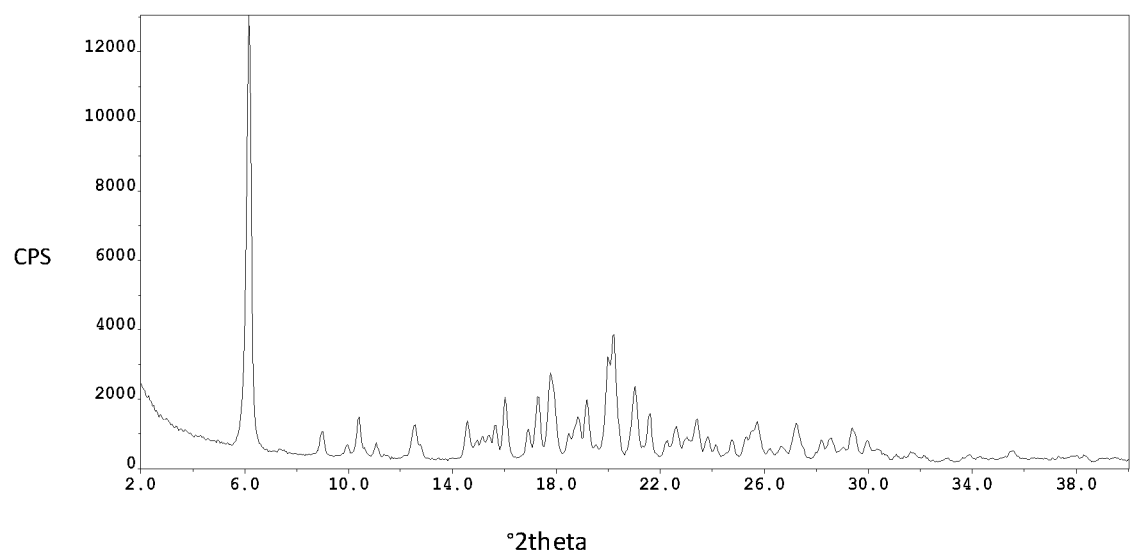

Figure 9: An X-ray powder diffractogram (XRPD) of form T4 of Valbenazine tosylate
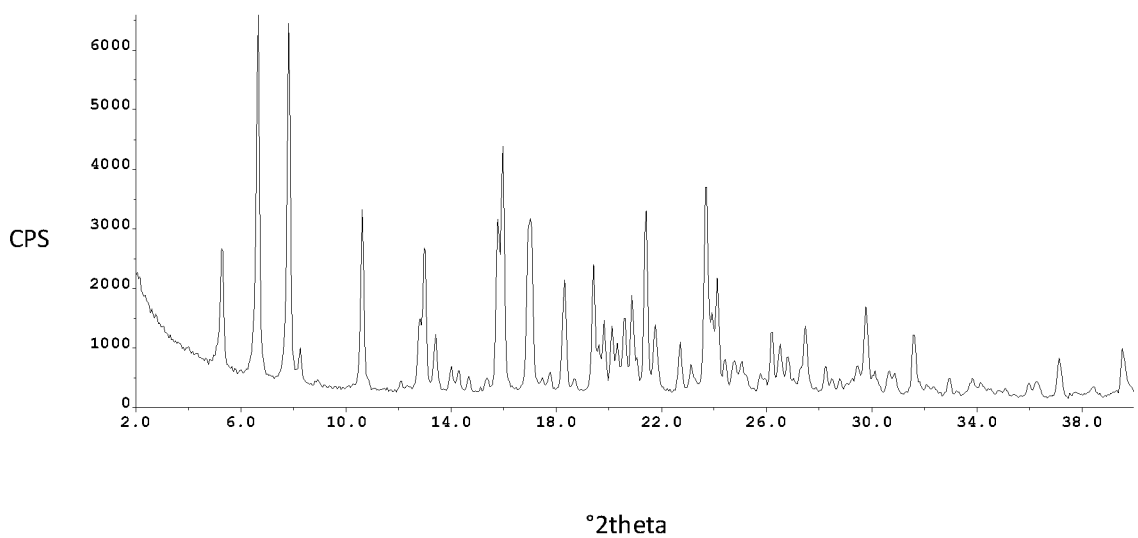

Figure 10: An X-ray powder diffractogram (XRPD) of form T5 of Valbenazine tosylate
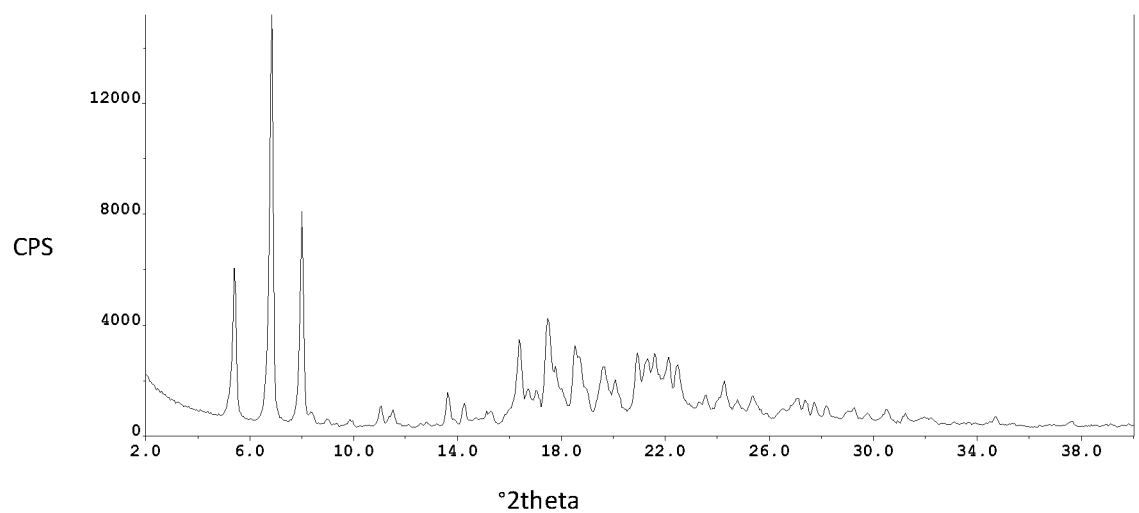

Figure 11: An X-ray powder diffractogram (XRPD) of form T6 of Valbenazine tosylate
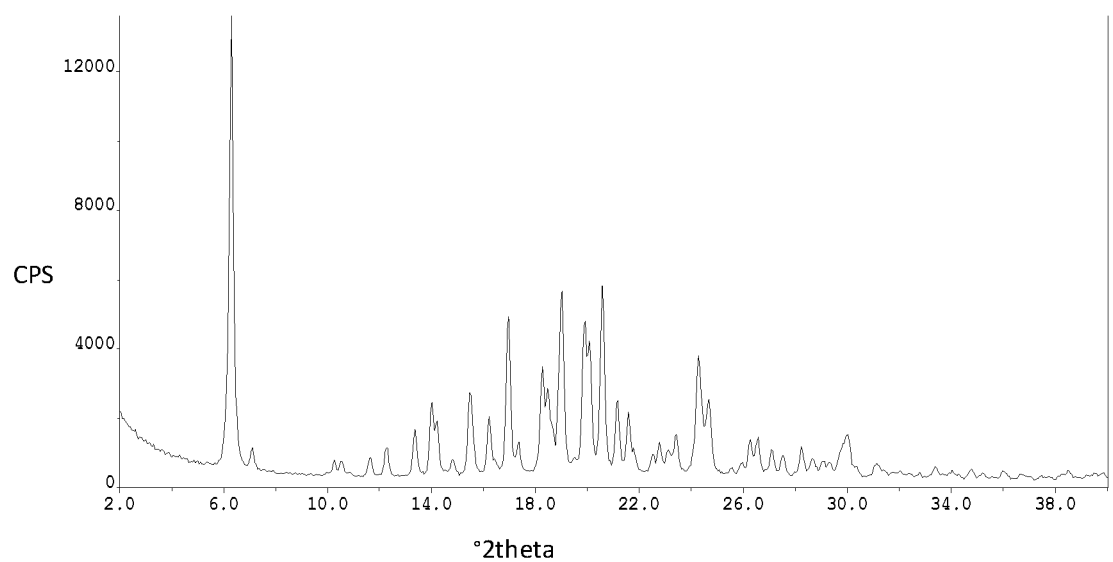

Figure 12: An X-ray powder diffractogram (XRPD) of form T7 of Valbenazine tosylate
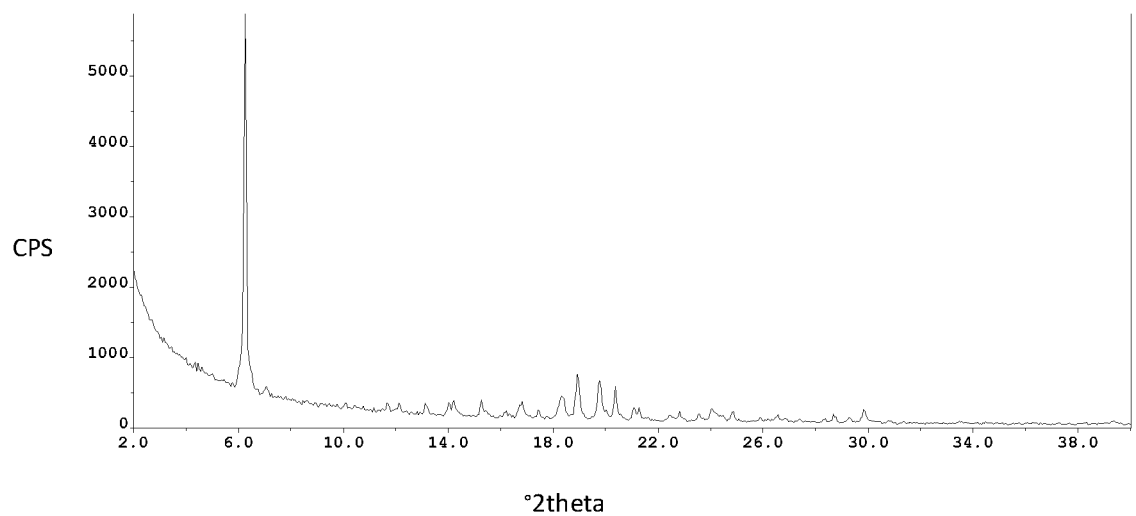

Figure 13: An X-ray powder diffractogram (XRPD) of form T8 of Valbenazine tosylate
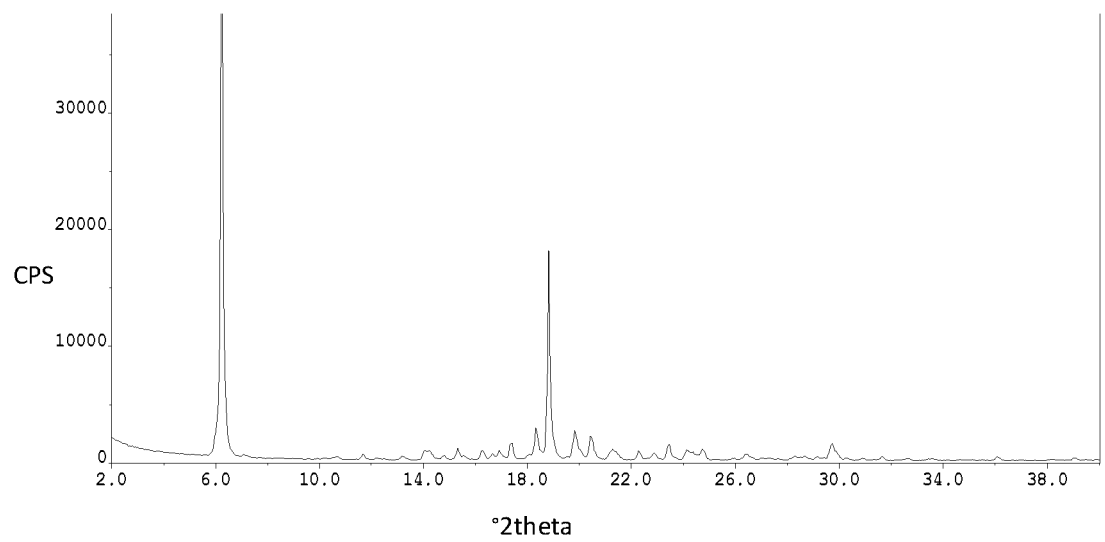

Figure 14: An X-ray powder diffractogram (XRPD) of form T9 of Valbenazine tosylate
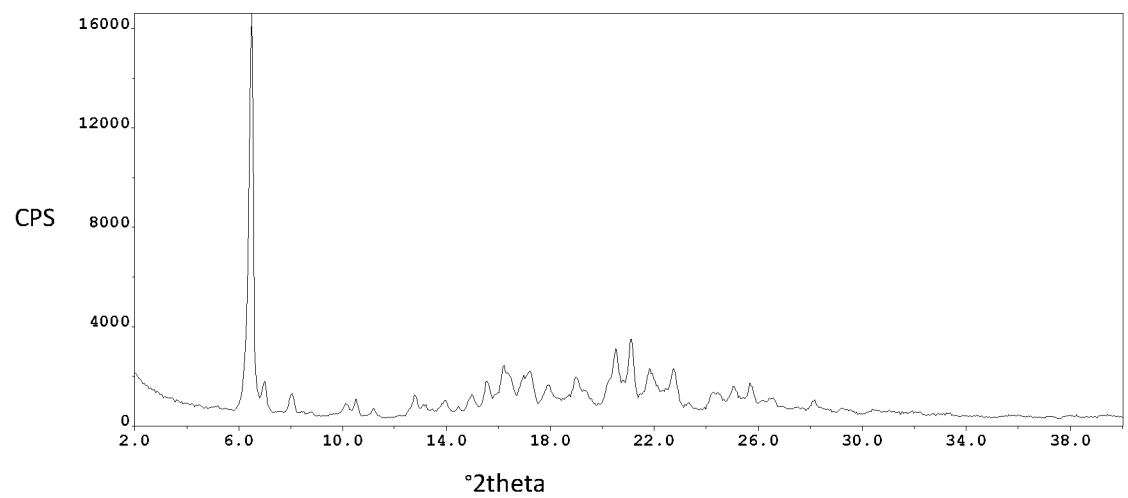

Figure 15: An X-ray powder diffractogram (XRPD) of form T10 of Valbenazine tosylate
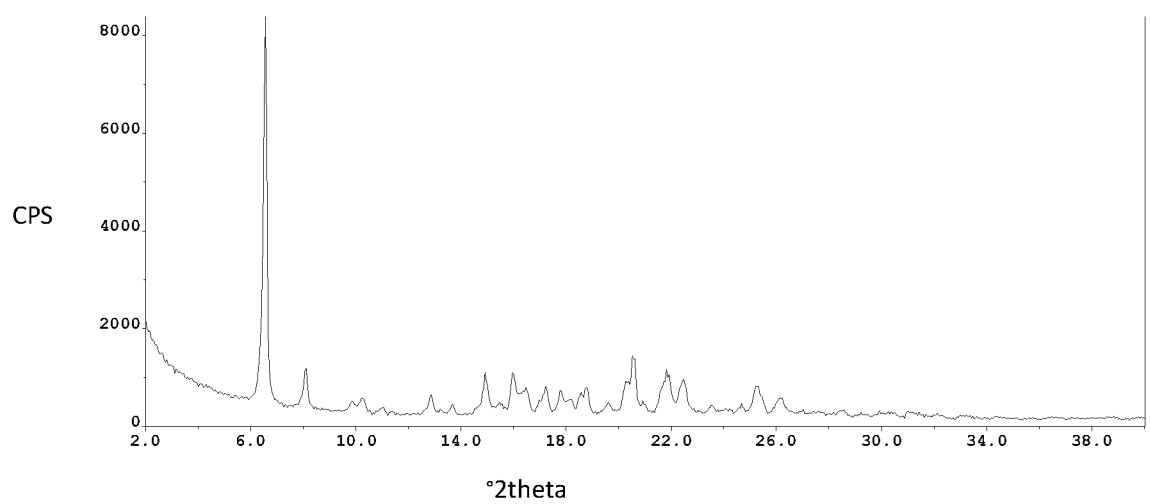

Figure 16: An X-ray powder diffractogram (XRPD) of T12 of Valbenazine tosylate
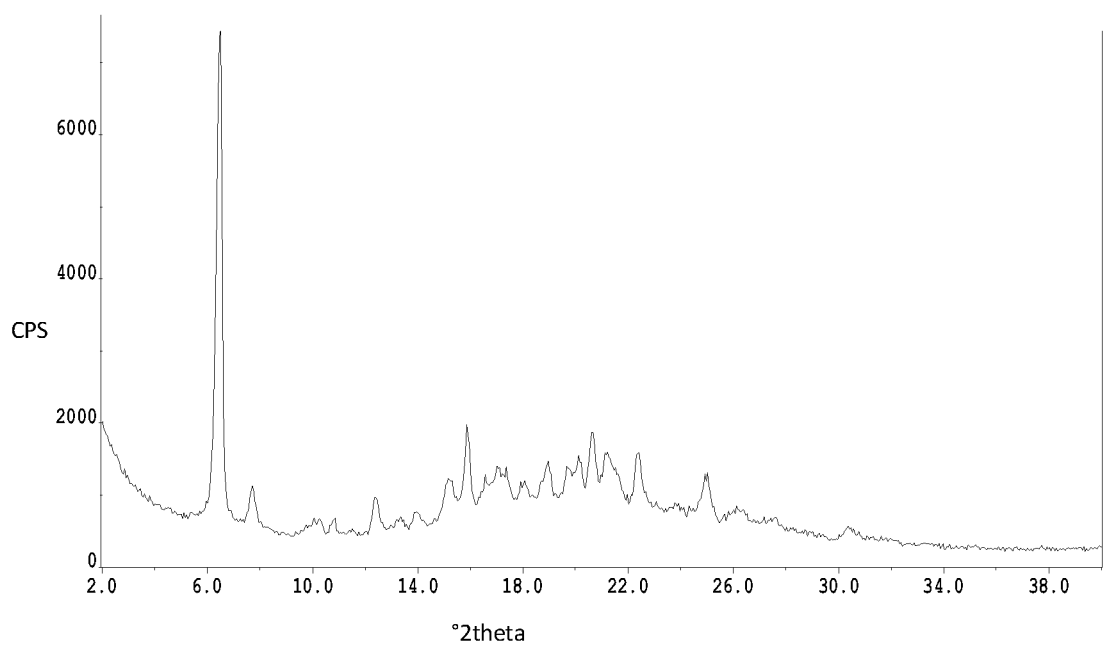

Figure 17: An X-ray powder diffractogram (XRPD) of F1 of Valbenazine fumarate
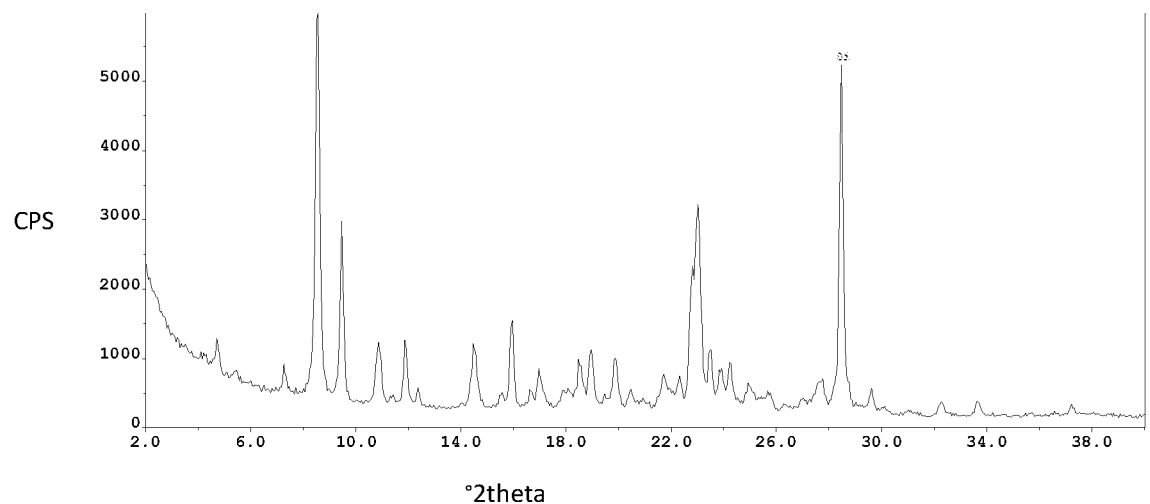
The strong peak at about 28.5 degrees (marked with Si) is attributed to silicon powder added as an internal standard.

Figure 18: An X-ray powder diffractogram (XRPD) of form S1 of Valbenazine stearate
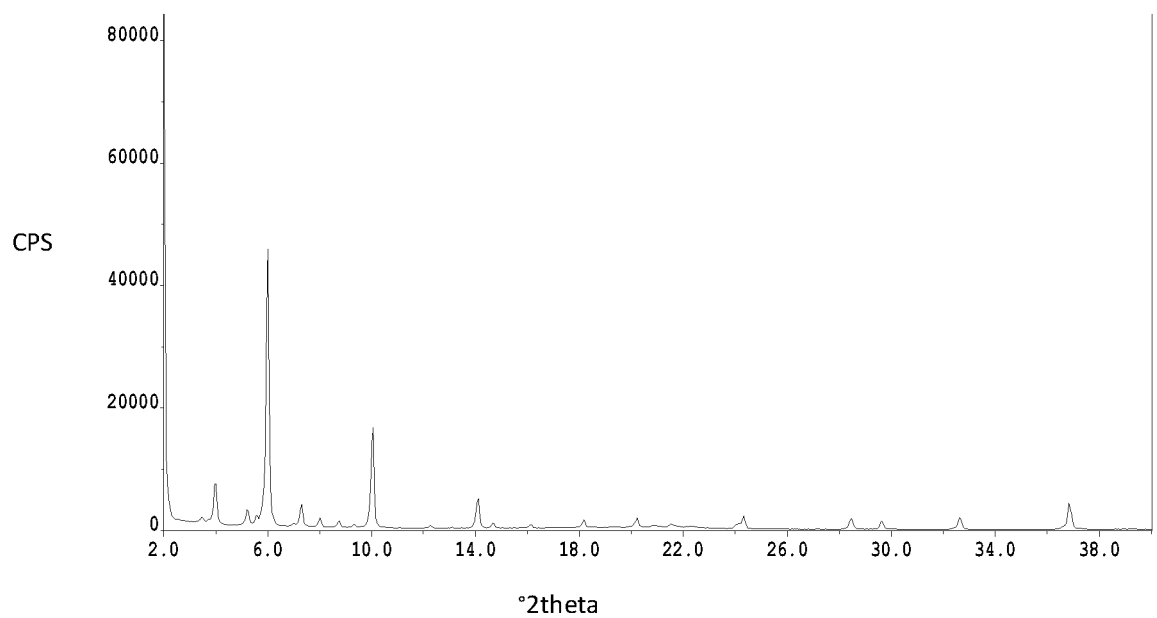

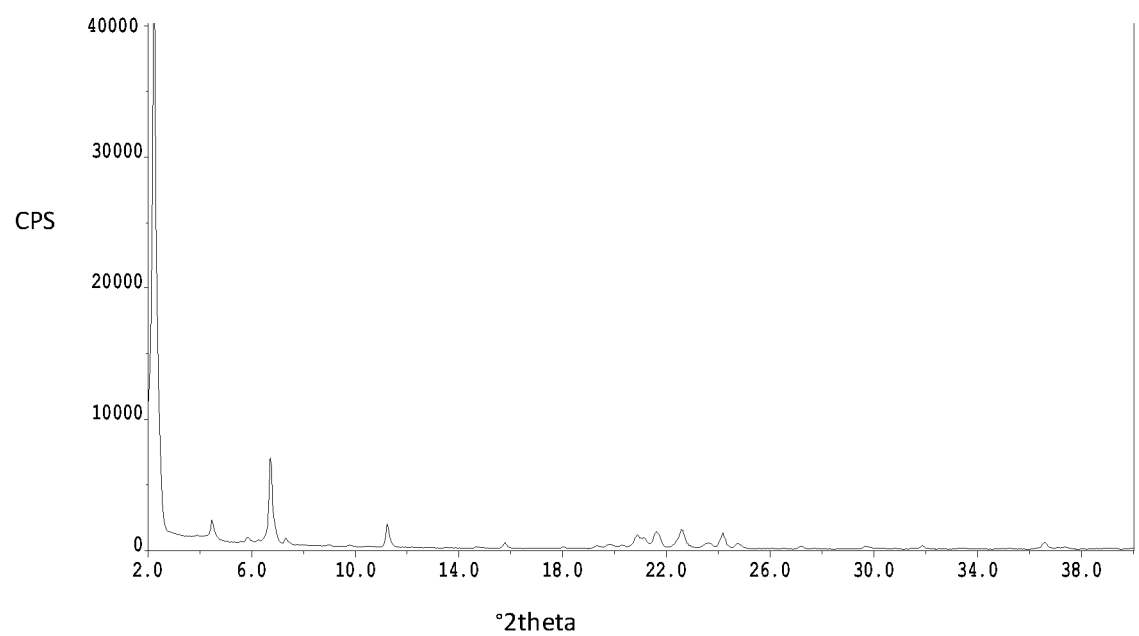
Figure 19: An X-ray powder diffractogram (XRPD) of form P1 of Valbenazine palmitate Figure 20: An X-ray powder diffractogram (XRPD) of form HS1 of Valbenazine sulfate
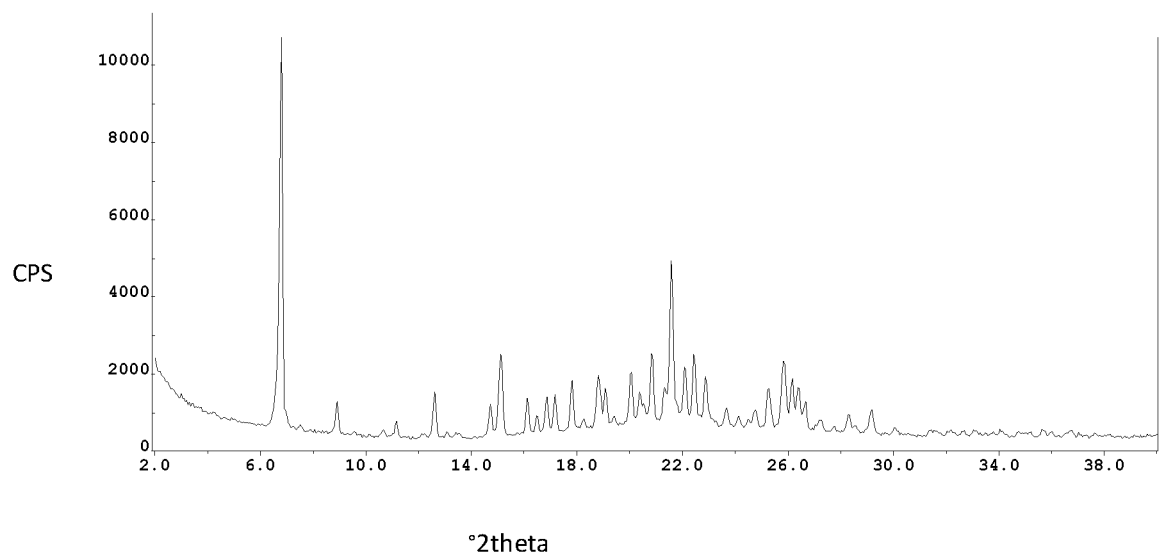

Figure 21: An X-ray powder diffractogram (XRPD) of form MS1 of Valbenazine mesylate
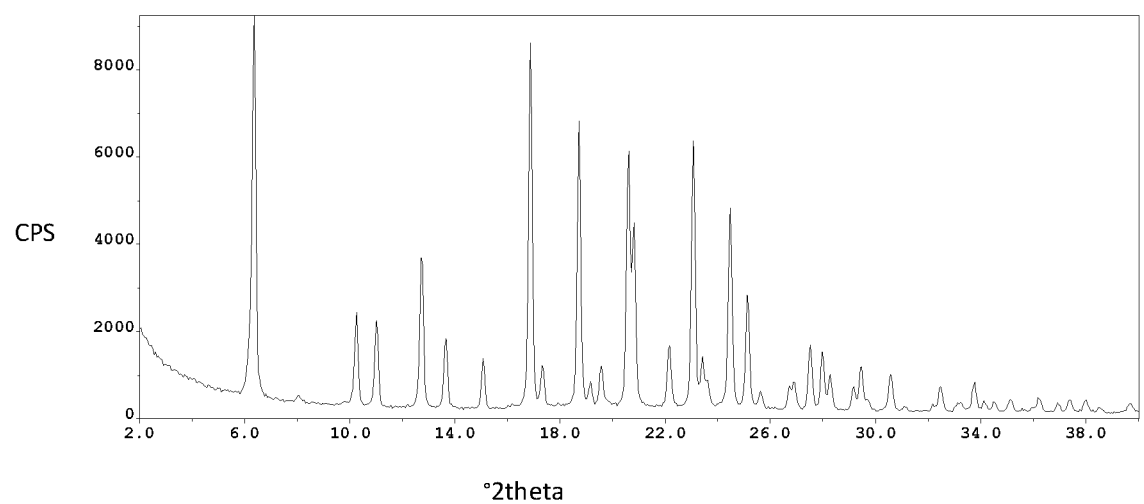

Figure 22: An X-ray powder diffractogram (XRPD) of mixture of form T10 and form T12 of Valbenazine tosylate
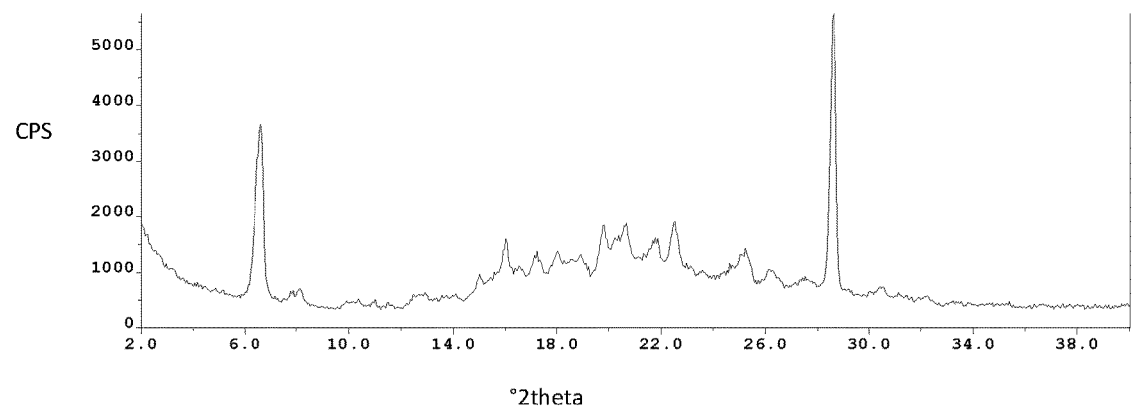
The peak at about 28.5° is attributed to silicon powder added as an internal standard.

A solid state $^{13}$C-NMR spectrum of from T10 of Valbenazine tosylate
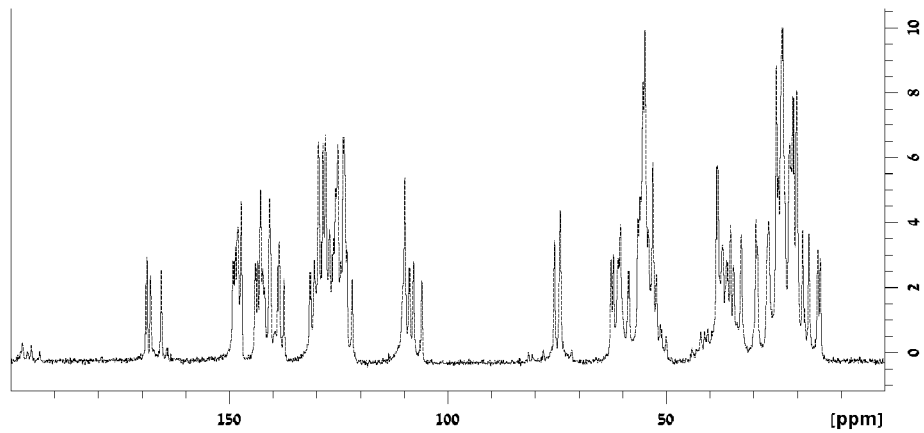
Figure 23A $^{13}$C-SS-NMR of Form T10 (0-200ppm)
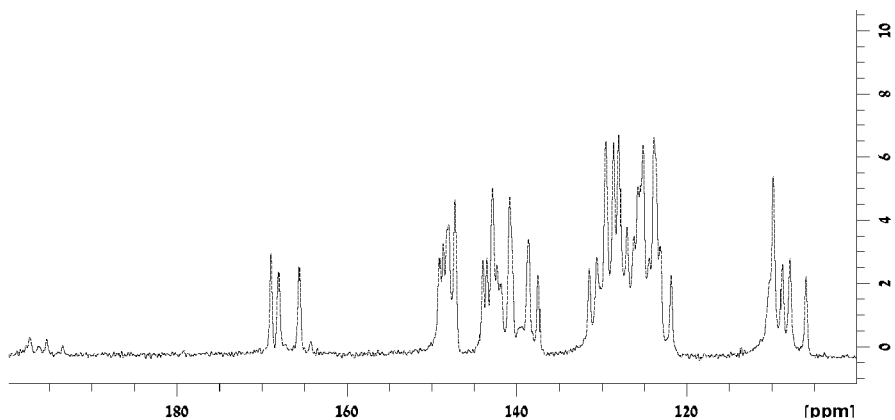
Figure 23B $^{13}$C-SS-NMR of Form T10 (100-200ppm)
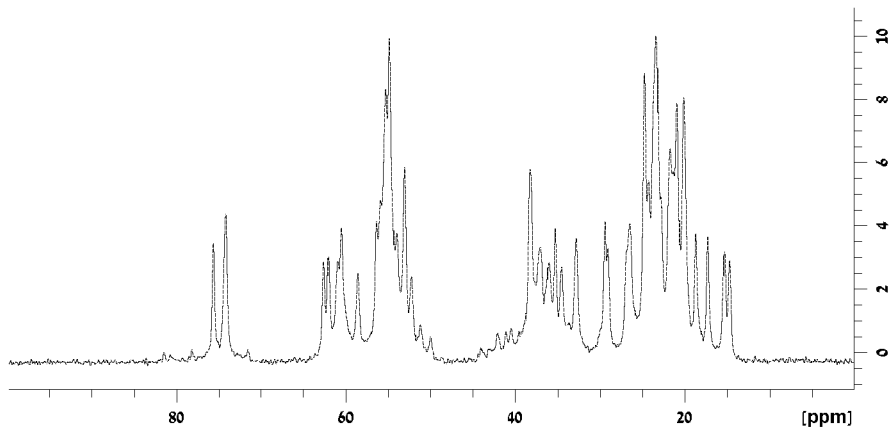
Figure 23C $^{13}$C-SS-NMR of Form T10 (0-100ppm)

Figure 24: An FT-IR spectrum of form T10 of Valbenazine tosylate
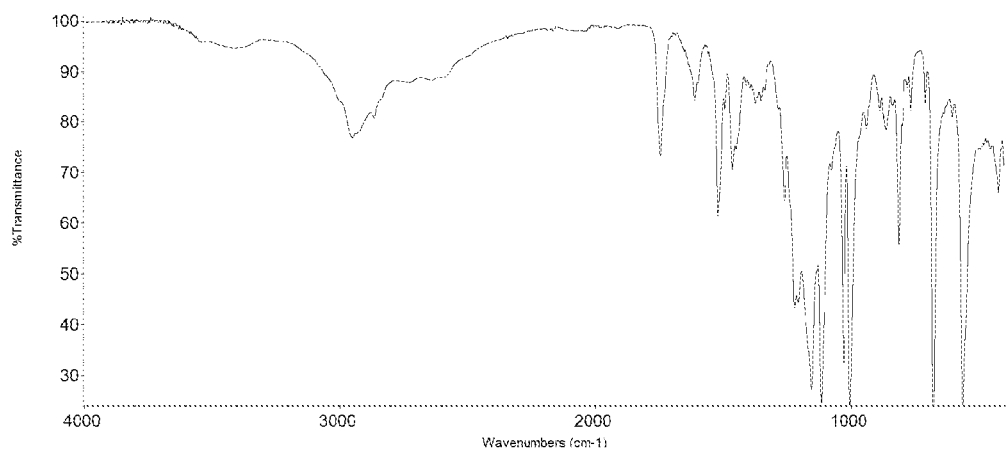

A solid state $^{13}$C-NMR spectrum of from T12 of Valbenazine tosylate
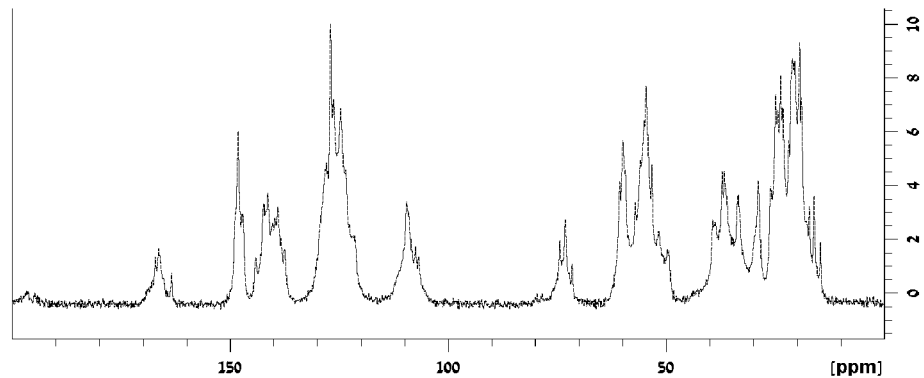
Figure 25A $^{13}$C-SS-NMR of Form T12 (0-200ppm)
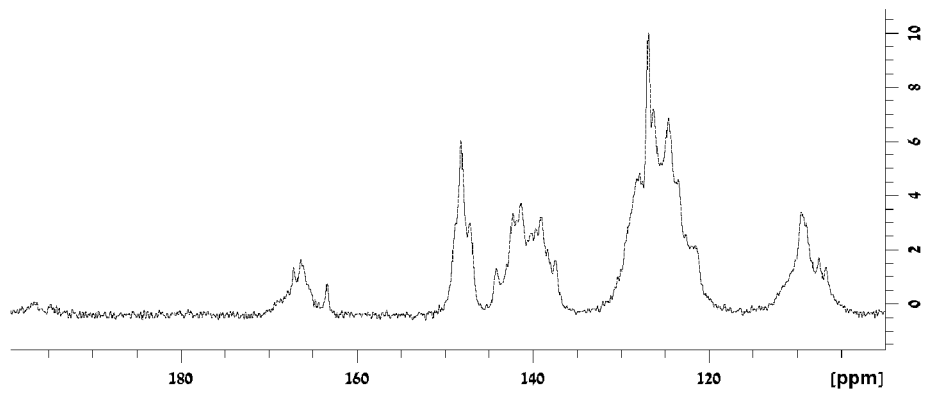
Figure 25B $^{13}$C-SS-NMR of Form T12 (100-200ppm)
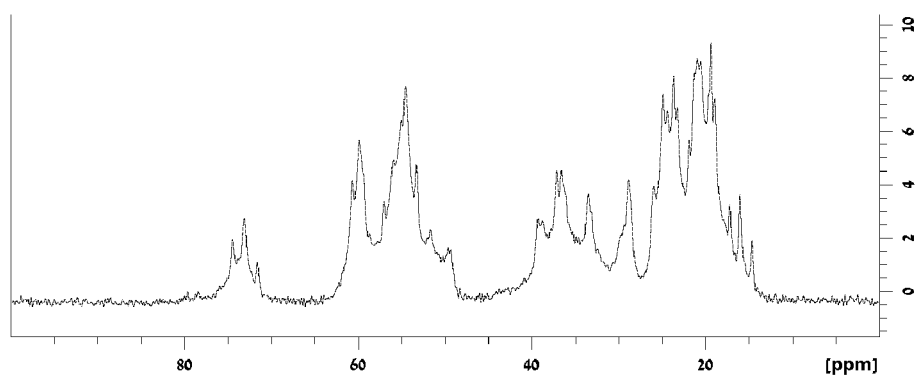
Figure 25C $^{13}$C-SS-NMR of Form T12 (0-100ppm)

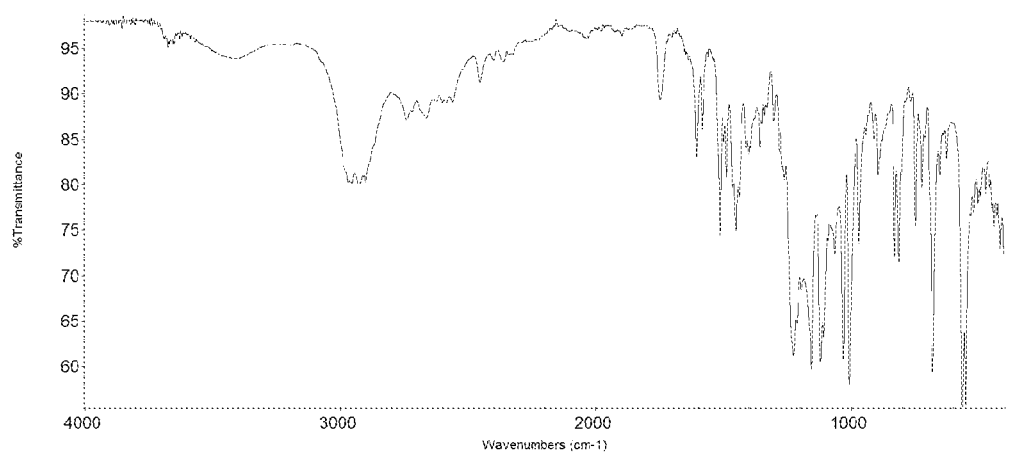
Figure 26: An FT-IR spectrum of form T12 of Valbenazine tosylate

Figure 27: X-ray powder diffractogram (XRPD) of form I of (+)-Tetrabenazine-(-)-DPTTA salt ((3R,11bR)-3-isobutyl-9,10-dimethoxy-2-oxo-1,2,3,4,5,6,7,11b-octahydropyrido[2,1-a]isoquinolin-5-ium (2S,3S)-3-carboxy-2,3-bis((4-methylbenzoyl)oxy)propanoate)
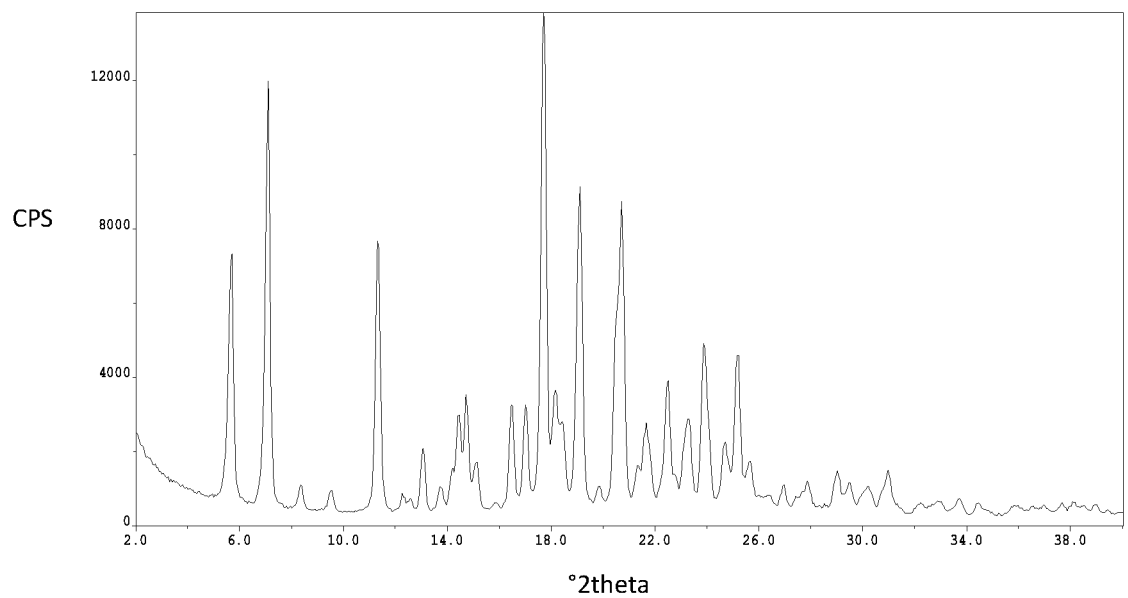

SOLID STATE FORMS OF VALBENAZINE

CROSS REFERENCE TO RELATED APPLICATIONS

This application is a National Stage of, and claims priority to and the benefit of, International Patent Application No. PCT/US2017/055561 filed on Oct. 6, 2017, which, in turn, claims the benefit of, and priority to, U.S. Provisional Patent Application No. 62/404,988, filed Oct. 6, 2016, U.S. Provisional Patent Application No. 62/406,173, filed Oct. 10, 2016, U.S. Provisional Patent Application No. 62/407,771, filed Oct. 13, 2016, U.S. Provisional Patent Application No. 62/424,216 filed Nov. 18, 2016, U.S. Provisional Patent Application No. 62/462,156, filed Feb. 22, 2017 and U.S. Provisional Patent Application No. 62/530,524, filed Jul. 10, 2017, the entire disclosures of each of which are incorporated by reference herein.

FIELD OF THE INVENTION

The present disclosure relates to solid state forms of Valbenazine, Valbenazine salts, processes for preparation thereof and pharmaceutical compositions thereof. The present disclosure further relates to processes for the preparation of Valbenazine and intermediates in the preparation thereof.

BACKGROUND OF THE INVENTION

Valbenazine has the chemical name (2R,3R,11bR)-3-isobutyl-9,10-dimethoxy-1,3,4,6,7,11b-hexahydro-2H-pyrido[2,1-a]isoquinolin-2-yl L-valinate.

Valbenazine has the following chemical structure:

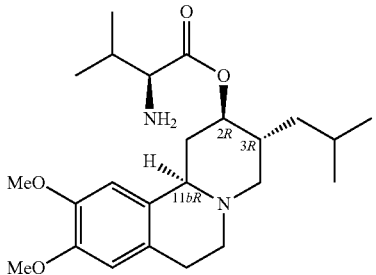 [SMILES: COc1cc2c(cc1OC)[C@H]1C[C@@H](OC(=O)[C@@H](N)C(C)C)[C@H](CC(C)C)CN1CC2]

Valbenazine is being developed by Neurocrine Bioscience for the treatment of a variety of central nervous system disorders, particularly involuntary hyperkinetic movement disorders such as drug-induced tardive dyskinesia and Tourette's syndrome. In the US, Phase III clinical trials are on-going for the treatment of drug-induced dyskinesia in patients with schizophrenia or schizoaffective disorder. Valbenazine is an inhibitor of vesicular monoamine transporter 2 (VMAT2).

Valbenazine is the active ingredient of the approved drug INGREZZA®, indicated for the treatment of adults with tardive dyskinesia. INGREZZA contains valbenazine, present as valbenazine tosylate salt, with the chemical name, L-Valine, (2R,3R,11bR)-1,3,4,6,7,11b-hexahydro-9,10-dimethoxy-3-(2-methylpropyl)-2H-benzo[a]quinolizin-2-yl ester, 4-methylbenzenesulfonate (1:2).

Valbenazine is disclosed in U.S. Pat. No. 8,039,627.

Valbenazine salts and polymorphs thereof are disclosed in WO2017/075340.

Polymorphism, the occurrence of different crystal forms, is a property of some molecules and molecular complexes. A single compound, like Valbenazine, may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD) pattern, infrared absorption fingerprint, Raman absorption fingerprint, and solid state ($^{13}$C-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts, solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New salts, polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life.

For at least these reasons, there is a need for additional solid state forms (including solvated forms or salts) of Valbenazine.

U.S. Pat. No. 8,039,627 describes a process for Valbenazine, as exemplified in Scheme 1.

Scheme 1: General Synthesis of Valbenazine

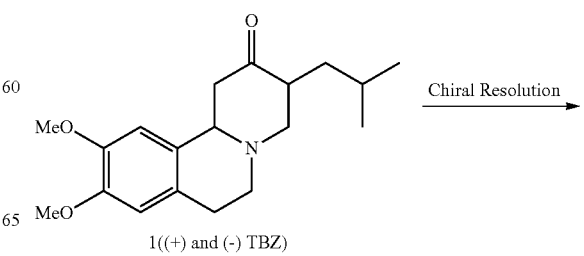

1((+) and (-) TBZ)

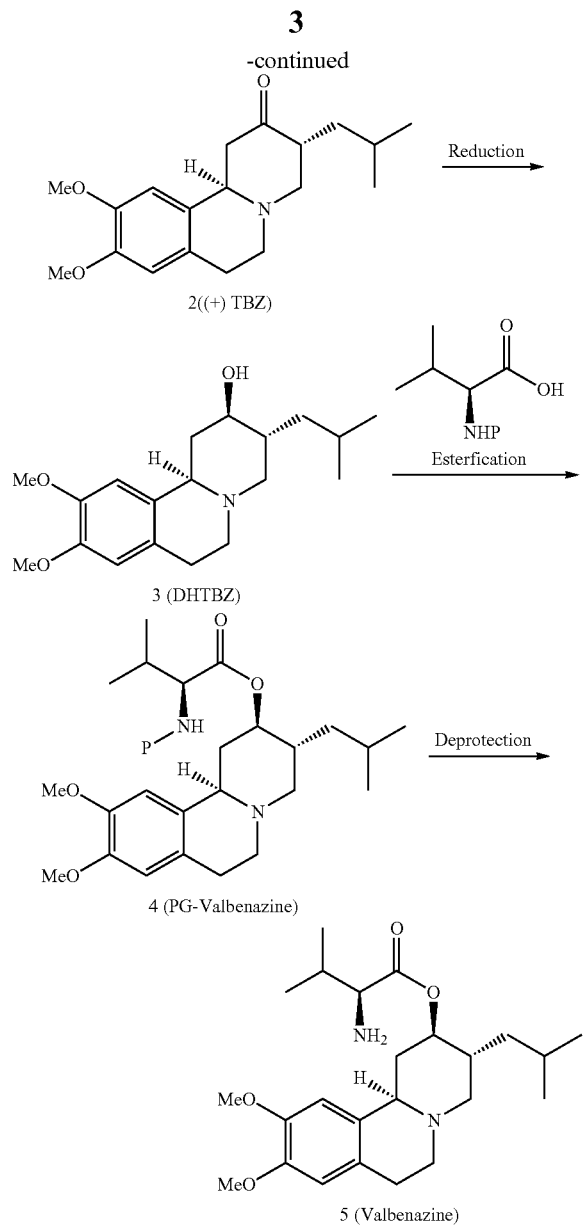

The process of U.S. Pat. No. 8,039,627 comprises a chromatographic chiral resolution of Tetrabenazine (Compound 1—(±)-TBZ), which is a racemic mixture of (R,R)- and (S,S)-enantiomers, to obtain the desired (R,R)-enantiomer of tetrabenazine (Compound 2—(+)-TBZ). Compound 2 is then reduced to (R,R,R)-Dihydrotetrabenazine (Compound 3—(R,R,R)-DHTBZ) and further converted to protected Valbenazine (Compound 4—PG-Valbenazine). Compound 4 is deprotected in order to generate Valbenazine (Compound 5).

The key intermediate of this process is (R,R,R)-Dihydrotetrabenazine (Compound 3—(R,R,R)-DHTBZ), hence the main challenge of this process is the chiral resolution of the initial racemic mixture of the Tetrabenazine drug (Compound 1—(±)-TBZ).

(R,R,R)-Dihydrotetrabenazine (Compound 3—(R,R,R)-DHTBZ) was found to be the active ingredient of the already known drug tetrabenazine (Compound 1) and processes for its preparation have been described in the literature.

WO2012000308, Eur. J. Med. Chem., 2011, 46, 1841-1848 and Med. Chem. Lett., 2010, 46, 105-109 describe a chiral resolution of Tetrabenazine by a formation of diastereomeric salts using (+)-Camphorsulfonic acid. This type of resolution showed very low yields and inconsistent results which makes it difficult to scale up.

WO2008058621 describes a chiral separation of Tetrabenazine using column chromatography, which is not feasible for scale up and industrial production.

WO2008154243, KR1102957, U.S. Pat. No. 8,993,766 and KR1409335 describe different asymmetric syntheses for the preparation of (R,R,R)-Dihydrotetrabenazine (Compound 3—(R,R,R)-DHTBZ). These processes either contain multiple synthetic steps, which ultimately lead to low yields of the desired compound 3 and/or show poor stereoselectivity. Further, these processes involve exotic and expensive reagents which are not suitable for scale-up processes.

WO2017112857 (US 20170183346) describes preparation of Valbenazine tosylate by converting Valbenazine HCl to Valbenazine tosylate. The described process involves reduction of Tetrabenazine (Compound 1—(+)(−)TBZ) to racemic Dihydrotetrabenazine, followed by optical resolution in order to obtain (R,R,R)-Dihydrotetrabenazine (Compound 3—(R,R,R)-DHTBZ).

For at least the above reasons, there is a need to have improved processes for preparing Valbenazine, with increased efficiency and reasonable cost that can be used for an industrial scale.

SUMMARY OF THE INVENTION

The present disclosure relates to solid state forms of Valbenazine, processes for preparation thereof, and pharmaceutical compositions comprising these solid state forms.

The present disclosure also relates to solid state forms of Valbenazine tosylate, processes for preparation thereof, and pharmaceutical compositions comprising these solid state forms. Valbenazine tosylate as used herein is (2R,3R,11bR)-3-isobutyl-9,10-dimethoxy-1,3,4,6,7,11b-hexahydro-2H-pyrido[2,1-a]isoquinolin-2-yl L-valinate di-tosylate.

The present invention also relates to solid state forms of Valbenazine fumarate, processes for preparation thereof, and pharmaceutical compositions comprising these solid state forms.

The present disclosure also relates to solid state forms of Valbenazine stearate, processes for preparation thereof, and pharmaceutical compositions comprising these solid state forms.

The present disclosure also relates to solid state forms of Valbenazine palmitate, processes for preparation thereof, and pharmaceutical compositions comprising these solid state forms.

The present disclosure also relates to solid state forms of Valbenazine sulfate, processes for preparation thereof, and pharmaceutical compositions comprising these solid state forms.

The present disclosure also relates to solid state forms of Valbenazine mesylate, processes for preparation thereof, and pharmaceutical compositions comprising these solid state forms.

The present disclosure also provides uses of the solid state forms of Valbenazine or salts thereof for preparing other solid state forms of Valbenazine, Valbenazine salts and solid state forms thereof.

The present disclosure also provides solid state forms of Valbenazine or Valbenazine salts of the present disclosure for uses in the preparation of other solid state forms of Valbenazine, Valbenazine salts and solid state forms thereof.

The present disclosure further provides processes for preparing other solid state forms of Valbenazine, Valbenazine salts and solid state forms thereof.

In another embodiment, the present disclosure encompasses the described solid state forms of Valbenazine or Valbenazine salts for uses in the preparation of pharmaceutical compositions and/or formulations, optionally for the treatment of a variety of central nervous system disorders, particularly involuntary hyperkinetic movement disorders such as drug-induced tardive dyskinesia and Tourette's syndrome. Particularly, the described solid state forms of Valbenazine or Valbenazine salts may be used in the preparation of pharmaceutical compositions and/or formulations for the treatment or prophylaxis of a central nervous system disorder, a symptom of a neurological disorder, particularly involuntary hyperkinetic movement disorders such as tardive dyskinesia, drug-induced tardive dyskinesia and Tourette's syndrome, Huntington's disease, chorea associated with Huntington's disease, hemiballismus, chorea, senile chorea, tic disorders, tardive dyskinesia, myoclonus, dystonia and Tourette's syndrome, tremor, dystonia, ballism, tics, akathisia, stereotypies, myoclonus and athetosis, and preferably for the treatment or prophylaxis of tardive dyskinesia, drug-induced tardive dyskinesia and Tourette's syndrome.

In another embodiment, the present disclosure encompasses uses of the described solid state form of Valbenazine or Valbenazine salts for the preparation of pharmaceutical compositions and/or formulations.

The present disclosure further provides pharmaceutical compositions comprising the solid state form of Valbenazine or Valbenazine salts according to the present disclosure.

In yet another embodiment, the present disclosure encompasses pharmaceutical formulations comprising the described solid state forms of Valbenazine or Valbenazine salts and at least one pharmaceutically acceptable excipient.

The present disclosure encompasses processes to prepare said pharmaceutical formulations of Valbenazine or Valbenazine salts comprising combining the described solid state form and at least one pharmaceutically acceptable excipient.

The solid state forms defined herein as well as the pharmaceutical compositions or formulations of the solid state form of Valbenazine or Valbenazine salts can be used as medicaments, particularly for the treatment of a variety of central nervous system disorders, particularly involuntary hyperkinetic movement disorders such as drug-induced tardive dyskinesia and Tourette's syndrome.

The present disclosure also provides methods of treating of a variety of central nervous system disorders, particularly involuntary hyperkinetic movement disorders such as drug-induced tardive dyskinesia and Tourette's syndrome, comprising administering a therapeutically effective amount of the solid state form of Valbenazine or Valbenazine salt of the present disclosure, or at least one of the herein described pharmaceutical compositions or formulations, to a subject suffering from of a central nervous system disorders, particularly involuntary hyperkinetic movement disorders such as drug-induced tardive dyskinesia and Tourette's syndrome, or otherwise in need of the treatment. Particularly, the present invention provides methods of treatment or prophylaxis of a central nervous system disorder, a symptom of a neurological disorder, particularly involuntary hyperkinetic movement disorders such as tardive dyskinesia, drug-induced tardive dyskinesia and Tourette's syndrome, Huntington's disease, chorea associated with Huntington's disease, hemiballismus, chorea, senile chorea, tic disorders, tardive dyskinesia, myoclonus, dystonia and Tourette's syndrome, tremor, dystonia, ballism, tics, akathisia, stereotypies, myoclonus and athetosis, and preferably for the treatment or prophylaxis of tardive dyskinesia, drug-induced tardive dyskinesia and Tourette's syndrome.

The present disclosure also provides uses of the solid state forms of Valbenazine or Valbenazine salts of the present disclosure, or at least one of the above pharmaceutical compositions or formulations for the manufacture of medicaments for treating central nervous system disorders, particularly involuntary hyperkinetic movement disorders such as drug-induced tardive dyskinesia and Tourette's syndrome.

The present disclosure further relates to processes for preparing Valbenazine or Valbenazine salts and intermediates in the preparation thereof.

The present disclosure provides an improved procedure for chiral resolution of Tetrabenazine (Compound 1) to obtain the pure (R,R)-enantiomer of Tetrabenazine ((+)-TBZ, Compound 2) using (−)-O,O'-Di-p-Toluoyl-L-Tartaric acid ((−)-DPTTA) as resolving agent.

Also provided is the crystalline form of (+)-Tetrabenazine-(−)-DPTTA salt ((3R,11bR)-3-isobutyl-9,10-dimethoxy-2-oxo-1,2,3,4,5,6,7,11b-octahydropyrido[2,1-a]isoquinolin-5-ium (2S,3S)-3-carboxy-2,3-bis((4-methylbenzoyl)oxy)propanoate).

In a further aspect, the present disclosure provides a process to obtain (R,R,R)-Dihydrotetrabenazine (Compound 3) by an asymmetric transfer hydrogenation (ATH) of a racemic mixture of (R,R)- and (S,S)-Tetrabenazine using a chiral catalyst, for example Ru(II) Noyori catalysts. In this way, (R,R,R)-Dihydrotetrabenazine (Compound 3) can be obtained using an asymmetric synthesis with only a few synthetic steps.

BRIEF DESCRIPTION OF THE FIGURES

FIG. 1 shows an X-ray powder diffractogram (XRPD) of form L1 of Valbenazine.

FIG. 2 shows an X-ray powder diffractogram (XRPD) of form L2 of Valbenazine.

FIG. 3 shows an X-ray powder diffractogram (XRPD) of form L3 of Valbenazine.

FIG. 4 shows an X-ray powder diffractogram (XRPD) of form L4 of Valbenazine.

FIG. 5 shows an X-ray powder diffractogram (XRPD) of form L2 of Valbenazine.

FIG. 6 shows an X-ray powder diffractogram (XRPD) of form T1 of Valbenazine tosylate.

FIG. 7 shows an X-ray powder diffractogram (XRPD) of form T2 of Valbenazine tosylate.

FIG. 8 shows an X-ray powder diffractogram (XRPD) of form T3 of Valbenazine tosylate.

FIG. 9 shows an X-ray powder diffractogram (XRPD) of form T4 of Valbenazine tosylate.

FIG. 10 shows an X-ray powder diffractogram (XRPD) of form T5 of Valbenazine tosylate.

FIG. 11 shows an X-ray powder diffractogram (XRPD) of form T6 of Valbenazine tosylate.

FIG. 12 shows an X-ray powder diffractogram (XRPD) of form T7 of Valbenazine tosylate.

FIG. 13 shows an X-ray powder diffractogram (XRPD) of form T8 of Valbenazine tosylate.

FIG. 14 shows an X-ray powder diffractogram (XRPD) of form T9 of Valbenazine tosylate.

FIG. 15 shows an X-ray powder diffractogram (XRPD) of form T10 of Valbenazine tosylate.

FIG. 16 shows an X-ray powder diffractogram (XRPD) of form T12 of Valbenazine tosylate.

FIG. 17 shows an X-ray powder diffractogram (XRPD) of form F1 of Valbenazine fumarate.

FIG. 18 shows an X-ray powder diffractogram (XRPD) of form S1 of Valbenazine stearate.

FIG. 19 shows an X-ray powder diffractogram (XRPD) of form P1 of Valbenazine palmitate.

FIG. 20 shows an X-ray powder diffractogram (XRPD) of form HS1 of Valbenazine sulfate.

FIG. 21 shows an X-ray powder diffractogram (XRPD) of form MS1 of Valbenazine mesylate.

FIG. 22 shows an X-ray powder diffractogram (XRPD) of mixture of form T10 and form T12 of Valbenazine tosylate.

FIG. 23 shows a solid state $^{13}$C-NMR spectrum of form T10 of Valbenazine tosylate (FIG. 23A, 0-200 ppm; FIG. 23B, 100-200 ppm; FIG. 23C, 0-100 ppm).

FIG. 24 shows an FT-IR spectrum of form T10 of Valbenazine tosylate.

FIG. 25 shows a solid state $^{13}$C-NMR spectrum of form T12 of Valbenazine tosylate (FIG. 25A, 0-200 ppm; FIG. 25B, 100-200 ppm; FIG. 25C, 0-100 ppm).

FIG. 26 shows an FT-IR spectrum of form T12 of Valbenazine tosylate.

FIG. 27 shows an X-ray powder diffractogram (XRPD) of form I of (+)Tetrabenazine-(−)-DPTTA salt ((3R,11bR)-3-isobutyl-9,10-dimethoxy-2-oxo-1,2,3,4,5,6,7,11b-octahydropyrido[2,1-a]isoquinolin-5-ium (2S,3S)-3-carboxy-2,3-bis((4-methylbenzoyl)oxy)propanoate).

DETAILED DESCRIPTION OF THE INVENTION

The present disclosure relates to a solid state form of Valbenazine, processes for preparation thereof and pharmaceutical compositions comprising this solid state form. The disclosure also relates to the conversion of the described solid state form of Valbenazine to other solid state forms of Valbenazine, Valbenazine salts and their solid state forms thereof.

The solid state form of Valbenazine according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

Further, the present disclosure relates to processes for the preparation of Valbenazine or Valbenazine salts and intermediates in the preparation thereof. Particularly, the disclosure relates to the novel compound (+)-Tetrabenazine-(−)-DPTTA salt ((3R,11bR)-3-isobutyl-9,10-dimethoxy-2-oxo-1,2,3,4,5,6,7,11b-octahydropyrido[2,1-a]isoquinolin-5-ium (2S,3S)-3-carboxy-2,3-bis((4-methylbenzoyl)oxy)propanoate), described hereinafter, processes for its preparation and its use as an intermediate in the preparation of Valbenazine or Valbenazine salts, and Valbenazine intermediates, such as (R,R,R)-Dihydrotetrabenazine (compound 3). The disclosure further encompasses a process for preparing Valbenazine comprising preparing any one or several of the above compounds according to the present disclosure and converting it to Valbenazine.

Particularly, the disclosure provides improved processes for the preparation of (R,R,R)-Dihydrotetrabenazine (compound 3), which uses inexpensive and commercially available starting materials. The processes of the present invention consist of simple reaction steps and avoid the use of expensive reagents and extreme hazardous reaction conditions. Therefore they can be used on an industrial scale.

The following definitions are used throughout this disclosure:

(±)-Tetrabenazine refers to a racemic mixture of (3R,11bR)-Tetrabenazine and (3S,11bS)-Tetrabenazine (compound 1).

(+)-Tetrabenazine refers to (3R,11bR)-Tetrabenazine (compound 2, (3R,11bR)-3-isobutyl-9,10-dimethoxy-1,3,4,6,7,11b-hexahydro-2H-pyrido[2,1-a]isoquinolin-2-one).

(−)-Tetrabenazine refers to (3S,11bS)-Tetrabenazine ((3S,11bS)-3-isobutyl-9,10-dimethoxy-1,3,4,6,7,11b-hexahydro-2H-pyrido[2,1-a]isoquinolin-2-one).

(−)-DPTTA refers to (−)-O—O'-Di-p-Toluoyl-L-Tartaric acid.

(R,R,R)-Dihydrotetrabenazine refers to (2R,3R,11bR)-Dihydrotetrabenazine (R,R,R)-DHTBZ, compound 3, (2R,3R,11bR)-3-isobutyl-9,10-dimethoxy-1,3,4,6,7,11b-hexahydro-2H-pyrido[2,1-a]isoquinolin-2-ol).

(S,R,R)-Dihydrotetrabenazine refers to (2S,3R,11bR)-Dihydrotetrabenazine (S,R,R)-DHTBZ, (2S,3R,11bR)-3-isobutyl-9,10-dimethoxy-1,3,4,6,7,11b-hexahydro-2H-pyrido[2,1-a]isoquinolin-2-ol)).

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Valbenazine referred to herein as being characterized by graphical data "as depicted in" a Figure will thus be understood to include any crystal forms of the Valbenazine, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% or less, about 10% or less, about 5% or less, about 2% or less, about 1% or less, or 0% of any other forms of the subject compound as measured, for example, by XRPD. Thus, the solid state form of Valbenazine described herein as substantially free of any other solid state forms would be understood to contain greater than about 80% (w/w), greater than about 90% (w/w), greater than about 95% (w/w), greater than about 98% (w/w), greater than about 99% (w/w), or 100% of the subject solid state form of Valbenazine. Accordingly, in some embodiments of the disclosure, the described solid state forms of Valbenazine may contain from about 1% to about 20% (w/w), from about 5% to about 20% (w/w), or from about 5% to about 10% (w/w) of one or more other solid state forms of the same Valbenazine.

As used herein, unless stated otherwise, XRPD peaks reported herein are optionally measured using CuK α radiation, λ=1.5418 Å.

As used herein, unless stated otherwise, solid state $^{13}C$ NMR chemical shifts reported herein are preferably measured using a magic angle spinning rate of 11 kHz, and at a temperature of 0° C.

As used herein, the term "isolated" in reference to solid state forms of Valbenazine of the present disclosure corresponds to solid state form of Valbenazine that is physically separated from the reaction mixture in which it is formed.

As used herein, Me-THF refers to 2-methyl-tetrahydrofuran, DCM refers to dichloromethane, EtOAc refers to ethylacetate and DMF refers to dimethylformamide.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, about 10 to about 18 hours, or about 16 hours.

As used herein, the expression "wet crystalline form" refers to a polymorph that was not dried using any conventional techniques to remove residual solvent. Examples for such conventional techniques can be, but not limited to, evaporation, vacuum drying, oven drying, drying under nitrogen flow, etc.

As used herein, the expression "dry crystalline form" refers to a polymorph that was dried using any conventional techniques to remove residual solvent. Examples of such conventional techniques can be, but are not limited to, evaporation, vacuum drying, oven drying, drying under nitrogen flow, etc.

As used herein, and unless stated otherwise, the term "anhydrous" in relation to crystalline Valbenazine relates to crystalline Valbenazine which does not include any crystalline water (or other solvents) in a defined, stoichiometric amount within the crystal. Moreover, an "anhydrous" form does not contain more than about 1% (w/w) of either water or organic solvents as measured for example by TGA.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount. The amount of solvent employed in a chemical process, e.g., a reaction or crystallization, may be referred to herein as a number of "volumes" or "vol" or "V." For example, a material may be referred to as being suspended in 10 volumes (or 10 vol or 10 V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding methyl tert-butyl ether (MTBE) (1.5 v/v) to a 100 ml reaction mixture would indicate that 150 mL of MTBE was added.

As used herein the term non-hygroscopic in relation to crystalline Valbenazine refers to less than about 0.2% (w/w) absorption of water at about 25° C. and about 80% relative humidity (RH) by the crystalline Valbenazine as determined for example by TGA. Water can be, for example, atmospheric water.

As used herein, the term "reduced pressure" refers to a pressure of about 10 mbar to about 50 mbar.

The present disclosure comprises a crystalline form of Valbenazine designated as Form L1. The crystalline Form L1 of Valbenazine can be characterized by data selected from one or more of the following: an XRPD pattern having peaks at 6.0, 6.8, 13.5, 16.8 and 18.1 degrees 2-theta±0.2 degrees 2-theta; an XRPD pattern as depicted in FIG. 1; and combinations of these data. Crystalline Form L1 of Valbenazine may be further characterized by the XRPD pattern having peaks at 6.0, 6.8, 13.5, 16.8 and 18.1 degrees 2-theta±0.2 degrees 2-theta, and also having one, two, three, four or five additional peaks selected from 12.0, 19.9, 20.3, 23.9 and 26.4 degrees 2-theta±0.2 degrees 2-theta.

Crystalline Form L1 of Valbenazine may be characterized by each of the above characteristics alone/or by all possible combinations, e.g. by XRPD pattern having peaks at 6.0, 6.8, 13.5, 16.8 and 18.1 degrees 2-theta±0.2 degrees 2-theta and an XRPD pattern as depicted in FIG. 1.

The present disclosure further comprises a crystalline form of Valbenazine designated as Form L2. The crystalline Form L2 of Valbenazine can be characterized by data selected from one or more of the following: an XRPD pattern having peaks at 4.6, 9.2, 14.8, 18.6 and 19.5 degrees 2-theta±0.2 degrees 2-theta; an XRPD pattern as depicted in FIG. 2 or in FIG. 5; and combinations of these data. Crystalline Form L2 of Valbenazine may be further characterized by the XRPD pattern having peaks at 4.6, 9.2, 14.8, 18.6 and 19.5 degrees 2-theta±0.2 degrees 2-theta, and also having one, two, three, four or five additional peaks selected from 4.2, 7.4, 5.7, 13.8 and 15.7 degrees 2-theta±0.2 degrees 2-theta. Alternatively, crystalline Form L2 of Valbenazine may be further characterized by the XRPD pattern having peaks at 4.6, 9.2, 14.8, 18.6 and 19.5 degrees 2-theta±0.2 degrees 2-theta, and also having one, two, three, four or five additional peaks selected from 10.1, 13.8, 17.7, 19.5, 22.3 degrees 2-theta±0.2 degrees 2-theta.

Crystalline Form L2 of Valbenazine may be characterized by each of the above characteristics alone/or by all possible combinations, e.g. by XRPD pattern having peaks at 4.6, 9.2, 14.8, 18.6 and 19.5 degrees 2-theta±0.2 degrees 2-theta and an XRPD pattern as depicted in FIG. 2.

The present disclosure further comprises a crystalline form of Valbenazine designated as Form L3. The crystalline Form L3 of Valbenazine can be characterized by data selected from one or more of the following: an XRPD pattern having peaks at 7.3, 8.0, 14.7, 29.6 and 32.5 degrees 2-theta±0.2 degrees 2-theta; an XRPD pattern as depicted in FIG. 3; and combinations of these data. Crystalline Form L3 of Valbenazine may be further characterized by the XRPD pattern having peaks at 7.3, 8.0, 14.7, 29.6 and 32.5 degrees 2-theta±0.2 degrees 2-theta, and also having one, two, three, four or five additional peaks selected from 16.1, 19.6, 22.1, 23.4 and 37.3 degrees 2-theta±0.2 degrees 2-theta.

Crystalline Form L3 of Valbenazine may be characterized by each of the above characteristics alone/or by all possible combinations, e.g. by XRPD pattern having peaks at 7.3, 8.0, 14.7, 29.6 and 32.5 degrees 2-theta±0.2 degrees 2-theta and an XRPD pattern as depicted in FIG. 3. The present disclosure also provides the use of the solid state form of Valbenazine for preparing other solid state forms of Valbenazine, Valbenazine salts and their solid state forms thereof.

The present disclosure further comprises a crystalline form of Valbenazine designated as Form L4. The crystalline Form L4 of Valbenazine can be characterized by data selected from one or more of the following: an XRPD pattern having peaks at 4.2, 5.7, 8.7 12.6 and 25.7 degrees 2-theta±0.2 degrees 2-theta; an XRPD pattern as depicted in FIG. 4; and combinations of these data. Crystalline Form L4 of Valbenazine may be further characterized by the XRPD pattern having peaks at 4.2, 5.7, 8.7, 12.6 and 25.7 degrees 2-theta±0.2 degrees 2-theta, and also having one, two, three, four or five additional peaks selected from 7.7, 12.3, 15.4, 17.3 and 18.5 degrees 2-theta±0.2 degrees 2-theta.

Crystalline Form L4 of Valbenazine may be characterized by each of the above characteristics alone/or by all possible combinations, e.g. by XRPD pattern having peaks at 4.2, 5.7, 8.7, 12.6 and 25.7 degrees 2-theta±0.2 degrees 2-theta and an XRPD pattern as depicted in FIG. 4. The present disclosure also provides the use of the solid state form of Valbenazine for preparing other solid state forms of Valbenazine, Valbenazine salts and their solid state forms thereof.

The present invention further encompasses Valbenazine ditosylate Me-THF solvate, Valbenazine ditosylate THF-solvate, and Valbenazine ditosylate isobutanol-solvate.

The present disclosure further comprises a crystalline form of Valbenazine tosylate designated as Form T1. The crystalline Form T1 of Valbenazine tosylate can be characterized by data selected from one or more of the following: an XRPD pattern having peaks at 5.7, 7.0, 7.6, 14.2 and 15.2 degrees 2-theta±0.2 degrees 2-theta; an XRPD pattern as depicted in FIG. 6; and combinations of these data. Crystalline Form T1 of Valbenazine tosylate may be further characterized by the XRPD pattern having peaks at 5.7, 7.0, 7.6, 14.2 and 15.2 degrees 2-theta±0.2 degrees 2-theta, and also having one, two, three, four or five additional peaks selected from 15.9, 16.9, 17.8, 18.5 and 22.5 degrees 2-theta±0.2 degrees 2-theta.

Crystalline Form T1 of Valbenazine tosylate may be characterized by each of the above characteristics alone/or by all possible combinations, e.g. by XRPD pattern having peaks at 5.7, 7.0, 7.6, 14.2 and 15.2 degrees 2-theta±0.2 degrees 2-theta and an XRPD pattern as depicted in FIG. 6. The present disclosure also provides the use of the solid state form of Valbenazine tosylate for preparing other solid state forms of Valbenazine, Valbenazine salts and their solid state forms thereof.

The present disclosure further comprises a crystalline form of Valbenazine tosylate designated as Form T2. The crystalline Form T2 of Valbenazine tosylate can be characterized by data selected from one or more of the following: an XRPD pattern having peaks at 6.2, 15.5, 16.5, 17.8, and 19.6 degrees 2-theta±0.2 degrees 2-theta; an XRPD pattern as depicted in FIG. 7; and combinations of these data. Crystalline Form T2 of Valbenazine tosylate may be further characterized by the XRPD pattern having peaks at 6.2, 15.5, 16.5, 17.8, and 19.6 degrees 2-theta±0.2 degrees 2-theta, and also having one, two, three, four or five additional peaks selected from 5.3, 18.3, 22.5, 22.9 and 24.5 degrees 2-theta±0.2 degrees 2-theta.

Crystalline Form T2 of Valbenazine tosylate may be characterized by each of the above characteristics alone/or by all possible combinations, e.g. by XRPD pattern having peaks at 6.2, 15.5, 16.5, 17.8, and 19.6 degrees 2-theta±0.2 degrees 2-theta and an XRPD pattern as depicted in FIG. 7. The present disclosure also provides the use of the solid state form of Valbenazine tosylate for preparing other solid state forms of Valbenazine, Valbenazine salts and their solid state forms thereof.

The present disclosure further comprises a crystalline form of Valbenazine tosylate designated as Form T3. The crystalline Form T3 of Valbenazine tosylate can be characterized by data selected from one or more of the following: an XRPD pattern having peaks at 6.1, 9.0, 14.6, 17.3 and 21.6 degrees 2-theta±0.2 degrees 2-theta; an XRPD pattern as depicted in FIG. 8; and combinations of these data. Crystalline Form T3 of Valbenazine tosylate may be further characterized by the XRPD pattern having peaks at 6.1, 9.0, 14.6, 17.3 and 21.6 degrees 2-theta±0.2 degrees 2-theta, and also having one, two, three, four or five additional peaks selected from 10.4, 16.0, 17.8, 20.2 and 21.0 degrees 2-theta±0.2 degrees 2-theta.

Crystalline Form T3 of Valbenazine tosylate may be characterized by each of the above characteristics alone/or by all possible combinations, e.g. by XRPD pattern having peaks at 6.1, 9.0, 14.6, 17.3 and 21.6 degrees 2-theta±0.2 degrees 2-theta and an XRPD pattern as depicted in FIG. 8. The present disclosure also provides the use of the solid state form of Valbenazine tosylate for preparing other solid state forms of Valbenazine, Valbenazine salts and their solid state forms thereof. Crystalline Form T3 of Valbenazine tosylate may be a solvate. Crystalline Form T3 may be a dioxane solvate. Crystalline Form T3 may be a Me-THF solvate. Crystalline Form T3 may further be characterized by a TGA thermogram showing a mass loss of about 5-7%. Crystalline form T3 may contain about 4.5% (w/w) of Me-THF.

The present disclosure further comprises a crystalline form of Valbenazine tosylate designated as Form T4. The crystalline Form T4 of Valbenazine tosylate can be characterized by data selected from one or more of the following: an XRPD pattern having peaks at 5.3, 6.6, 7.8, 13.4, and 19.4 degrees 2-theta±0.2 degrees 2-theta; an XRPD pattern as depicted in FIG. 9; and combinations of these data. Crystalline Form T4 of Valbenazine tosylate may be further characterized by the XRPD pattern having peaks at 5.3, 6.6, 7.8, 13.4, and 19.4 degrees 2-theta±0.2 degrees 2-theta, and also having one, two, three, four or five additional peaks selected from 10.6, 13.0, 21.4, 23.7, and 24.1 degrees 2-theta±0.2 degrees 2-theta, or selected from 10.6, 12.8, 15.8, 21.4 and 23.7 degrees 2-theta±0.2 degrees 2-theta Crystalline Form T4 of Valbenazine tosylate may be characterized by each of the above characteristics alone/or by all possible combinations, e.g. by an XRPD pattern having peaks at 5.3, 6.6, 7.8, 13.4, and 19.4 degrees 2-theta±0.2 degrees 2-theta and an XRPD pattern as depicted in FIG. 9. The present disclosure also provides the use of the solid state form of Valbenazine tosylate for preparing other solid state forms of Valbenazine, Valbenazine salts and their solid state forms thereof.

The present disclosure further comprises a crystalline form of Valbenazine tosylate designated as Form T5. The crystalline Form T5 of Valbenazine tosylate can be characterized by data selected from one or more of the following: an XRPD pattern having peaks at 10.9, 11.4, 16.3, 17.4 and 22.3 degrees 2-theta±0.2 degrees 2-theta; an XRPD pattern as depicted in FIG. 10; and combinations of these data. Crystalline Form T5 of Valbenazine tosylate may be further characterized by the XRPD pattern having peaks at 10.9, 11.4, 16.3, 17.4 and 22.3 degrees 2-theta±0.2 degrees 2-theta, and also having one, two, three, four or five additional peaks selected from 6.8, 16.9, 17.9, 21.8 and 25.3 degrees 2-theta±0.2 degrees 2-theta.

Crystalline Form T5 of Valbenazine tosylate may be characterized by each of the above characteristics alone/or by all possible combinations, e.g. by an XRPD pattern having peaks at 10.9, 11.4, 16.3, 17.4 and 22.3 degrees 2-theta±0.2 degrees 2-theta and an XRPD pattern as depicted in FIG. 10. The present disclosure also provides the use of the solid state form of Valbenazine tosylate for preparing other solid state forms of Valbenazine, Valbenazine salts and their solid state forms thereof.

The present disclosure further comprises a crystalline form of Valbenazine tosylate designated as Form T6. The crystalline Form T6 of Valbenazine tosylate can be characterized by data selected from one or more of the following: an XRPD pattern having peaks at 6.3, 12.3, 13.4, 14.0, and 15.5 degrees 2-theta±0.2 degrees 2-theta; an XRPD pattern as depicted in FIG. 11; and combinations of these data. Crystalline Form T6 of Valbenazine tosylate may be further characterized by the XRPD pattern having peaks at 6.3, 12.3, 13.4, 14.0, and 15.5 degrees 2-theta±0.2 degrees 2-theta, and also having one, two, three, four or five additional peaks selected from 16.9, 18.3, 20.6, 21.6, and 24.3 degrees 2-theta±0.2 degrees 2-theta.

Crystalline Form T6 of Valbenazine tosylate may be characterized by each of the above characteristics alone/or by all possible combinations, e.g. by an XRPD pattern having peaks at 6.3, 12.3, 13.4, 14.0, and 15.5 degrees 2-theta±0.2 degrees 2-theta and an XRPD pattern as depicted in FIG. 11. The present disclosure also provides the use of the solid state form of Valbenazine tosylate for preparing other solid state forms of Valbenazine, Valbenazine salts and their solid state forms thereof.

Crystalline Form T6 of Valbenazine tosylate may be a solvate. Crystalline Form T6 may be a tetrahydrofuran (THF) solvate. Crystalline Form T6 may further be characterized by a TGA thermogram showing a mass loss of about 6-7.5% when heated between 25-250° C.

The present disclosure further comprises a crystalline form of Valbenazine tosylate designated as Form T7. The crystalline Form T7 of Valbenazine tosylate can be characterized by data selected from one or more of the following: an XRPD pattern having peaks at 6.3, 11.7, 13.1, 14.0, and 18.9 degrees 2-theta±0.2 degrees 2-theta an XRPD pattern as depicted in FIG. 12; and combinations of these data. Crystalline Form T7 of Valbenazine tosylate may be further characterized by the XRPD pattern having peaks at 6.3, 11.7, 13.1, 14.0, and 18.9 degrees 2-theta±0.2 degrees 2-theta, and also having one, two, three, four or five additional peaks selected from 12.1, 14.2, 17.4, 18.3, and 19.8 degrees 2-theta±0.2 degrees 2-theta.

Crystalline Form T7 of Valbenazine tosylate may be characterized by each of the above characteristics alone/or by all possible combinations, e.g. by an XRPD pattern having peaks at 6.3, 11.7, 13.1, 14.0, and 18.9 degrees 2-theta±0.2 degrees 2-theta and an XRPD pattern as depicted in FIG. 12. The present disclosure also provides the use of the solid state form of Valbenazine tosylate for preparing other solid state forms of Valbenazine, Valbenazine salts and their solid state forms thereof.

Crystalline Form T7 of Valbenazine tosylate may be a solvate. Crystalline Form T7 may be an isobutanol solvate. Crystalline form T7 may further be characterized having a TGA showing a mass loss of 7-9% when heated between 25-250° C. Crystalline form T7 may contain about 7-8% (w/w) of isobutanol.

The present disclosure further comprises a crystalline form of Valbenazine tosylate designated as Form T8. The crystalline Form T8 of Valbenazine tosylate can be characterized by data selected from one or more of the following: an XRPD pattern having peaks at 6.2, 11.7, 13.2, 14.0, and 18.8 degrees 2-theta±0.2 degrees 2-theta; an XRPD pattern as depicted in FIG. 13; and combinations of these data. Crystalline Form T8 of Valbenazine tosylate may be further characterized by the XRPD pattern having peaks at 6.2, 11.7, 13.2, 14.0, and 18.8 degrees 2-theta±0.2 degrees 2-theta, and also having one, two, three, four or five additional peaks selected from 14.8, 17.4, 18.4, 20.4, and 22.3 degrees 2-theta±0.2 degrees 2-theta.

Crystalline Form T8 of Valbenazine tosylate may be characterized by each of the above characteristics alone/or by all possible combinations, e.g. by an XRPD pattern having peaks at 6.2, 11.7, 13.2, 14.0, and 18.8 degrees 2-theta±0.2 degrees 2-theta and an XRPD pattern as depicted in FIG. 13. The present disclosure also provides the use of the solid state form of Valbenazine tosylate for preparing other solid state forms of Valbenazine, Valbenazine salts and their solid state forms thereof.

Crystalline Form T8 of Valbenazine tosylate may be a solvate. Crystalline Form T8 may be a dioxane solvate.

The present disclosure further comprises a crystalline form of Valbenazine tosylate designated as Form T9. The crystalline Form T9 of Valbenazine tosylate can be characterized by data selected from one or more of the following: an XRPD pattern having peaks at 6.4, 6.9, 8.0, 10.4, and 15.5 degrees 2-theta±0.2 degrees 2-theta; an XRPD pattern as depicted in FIG. 14; and combinations of these data. Crystalline Form T9 of Valbenazine tosylate may be further characterized by the XRPD pattern having peaks at 6.4, 6.9, 8.0, 10.4, and 15.5 degrees 2-theta±0.2 degrees 2-theta, and also having one, two, three, four or five additional peaks selected from 13.9, 18.9, 21.0, 22.7, and 25.6 degrees 2-theta±0.2 degrees 2-theta.

Crystalline Form T9 of Valbenazine tosylate may be characterized by each of the above characteristics alone/or by all possible combinations, e.g. by an XRPD pattern having peaks at 6.4, 6.9, 8.0, 10.4, and 15.5 degrees 2-theta±0.2 degrees 2-theta and an XRPD pattern as depicted in FIG. 14. The present disclosure also provides the use of the solid state form of Valbenazine tosylate for preparing other solid state forms of Valbenazine, Valbenazine salts and their solid state forms thereof.

The present disclosure further comprises a crystalline form of Valbenazine tosylate designated as Form T10. The crystalline Form T10 of Valbenazine tosylate can be characterized by data selected from one or more of the following: an XRPD pattern having peaks at 6.4, 8.0, 10.9, 15.9 and 22.4 degrees 2-theta±0.2 degrees 2-theta; an XRPD pattern as depicted in FIG. 15; and combinations of these data. Crystalline Form T10 of Valbenazine tosylate may alternatively or additionally be characterized by data selected from one or more of the following: a solid state $^{13}$C-NMR spectrum with peaks at 168.9, 165.5, 147.2, 106.0 and 75.6 ppm±0.2 ppm; or by a solid state $^{13}$C-NMR spectrum having the following chemical shift absolute differences from a peak at 53.0±1 ppm of 115.9, 112.5, 94.2, 53.0 and 22.6±0.1 ppm; or by a solid state $^{13}$C-NMR spectrum substantially as depicted in FIG. 23; or combinations of these data.

Crystalline form T10 of Valbenazine tosylate may be further characterized by the XRPD pattern having peaks at 6.4, 8.0, 10.9, 15.9 and 22.4 degrees 2-theta±0.2 degrees 2-theta, and also having one, two, three, four or five additional peaks selected from 9.8, 13.6, 14.8, 18.7, and 20.5 degrees 2-theta±0.2 degrees 2-theta.

Crystalline form T10 of Valbenazine tosylate may be further characterized by data selected from one of the following: an FT-IR spectrum having one, two, three, four or more peaks selected from 2953, 2867, 1747, 1613, 1522, 1465, 1262, 1156, 1118, and 1006 cm$^{-1}$±2 cm$^{-1}$; an FT-IR spectrum as depicted in FIG. 24, and combinations of these data.

Crystalline Form T10 of Valbenazine tosylate may be characterized by each of the above characteristics alone/or by all possible combinations, e.g. by an XRPD pattern having peaks at 6.4, 8.0, 10.9, 15.9 and 22.4 degrees 2-theta±0.2 degrees 2-theta and an XRPD pattern as depicted in FIG. 15.

Crystalline Form T10 of Valbenazine tosylate may alternatively or additionally be characterized by a XRPD pattern having peaks at: 6.4, 8.0, 9.8, 10.1, 10.9, 12.7, 13.1, 13.6, 14.8, 15.3, 15.9, 16.3, 17.1, 17.6, 18.0, 18.7, 19.5, 20.5, 20.8, 21.7, 22.4, 22.9, 23.4, 23.9, 24.1, 24.5, 25.1, 26.1, 26.9, 27.5, 28.4, 29.1, 29.8, 30.2, 30.9, 31.3, 32.0, and 33.0 degrees 2-theta±0.2 degrees 2-theta.

The present disclosure also provides the use of the solid state form of Valbenazine tosylate for preparing other solid state forms of Valbenazine, Valbenazine salts and their solid state forms thereof.

The present disclosure further comprises a crystalline form of Valbenazine tosylate designated as Form T12. The crystalline Form T12 of Valbenazine tosylate can be characterized by data selected from one or more of the following: an XRPD pattern having peaks at 6.4, 7.6, 12.3, 15.2 and 24.9 degrees 2-theta±0.2 degrees 2-theta; an XRPD pattern as depicted in FIG. 16; and combinations of these data. Crystalline Form T12 of Valbenazine tosylate may alternatively or additionally be characterized by data selected from one or more of the following: a solid state $^{13}$C-NMR spectrum with peaks at 166.4, 148.1, 126.9, 109.5 and 73.1 ppm±0.2 ppm; or by a solid state $^{13}$C-NMR spectrum having the following chemical shift absolute differences from a peak at 54.5±1 ppm of 111.9, 93.6, 72.4, 55.0 and 18.6±0.1 ppm; or by a solid state $^{13}$C-NMR spectrum substantially as depicted in FIG. 25; or combinations of these data.

Crystalline Form T12 of Valbenazine tosylate may be further characterized by the XRPD pattern having peaks at 6.4, 7.6, 12.3, 15.2 and 24.9 degrees 2-theta±0.2 degrees 2-theta, and also having one, two, three, four or five additional peaks selected from 10.8, 13.9, 15.8, 18.9 and 22.3 degrees 2-theta±0.2 degrees 2-theta. Crystalline Form T12 of Valbenazine may be further characterized by absence of one, two, three or four peaks selected from 5.3, 5.7, 6.9 and 12.8 degrees 2-theta±0.2 degrees 2-theta.

Crystalline form T12 of Valbenazine tosylate may be further characterized by data selected from one of the following: an FT-IR spectrum having one, two, three, four or more peaks selected from 2931, 2740, 2663, 2453, 1748, 1606, 1584, 1452, 1227 and 1008 cm$^{-1}$±2 cm$^{-1}$; an FT-IR spectrum as depicted in FIG. 26, and combinations of these data.

Crystalline Form T12 of Valbenazine tosylate may alternatively or additionally be characterized by a XRPD pattern having peaks at: 6.4, 7.6, 8.2, 9.7, 10.0, 10.2, 10.8, 11.4, 11.7, 12.3, 13.3, 13.9, 15.2, 15.8, 16.5, 16.9, 17.3, 18.0, 18.9, 19.6, 20.0, 20.5, 21.1, 22.3, 23.0, 23.8, 24.2, 24.9, 25.6, 26.0, 27.1, 27.5, 28.2, 28.6, 28.9, 29.2, 29.3, 30.3, 31.0, 31.2, 31.5, 32.6, 32.8, and 33.2 degrees 2-theta±0.2 degrees 2-theta.

Crystalline Form T12 of Valbenazine tosylate may be characterized by each of the above characteristics alone/or by all possible combinations, e.g. by an XRPD pattern having peaks at 6.4, 7.6, 12.3, 15.2 and 24.9 degrees 2-theta±0.2 degrees 2-theta and an XRPD pattern as depicted in FIG. 16. The present disclosure also provides the use of the solid state form of Valbenazine tosylate for preparing other solid state forms of Valbenazine, Valbenazine salts and their solid state forms thereof.

The present invention further encompasses Valbenazine fumarate, Valbenazine stearate, Valbenazine palmitate, Valbenazine sulfate, and Valbenazine mesylate.

In one embodiment, the present disclosure further comprises a crystalline form of Valbenazine fumarate designated as Form F1. The crystalline Form F1 of Valbenazine fumarate can be characterized by data selected from one or more of the following: an XRPD pattern having peaks at 4.7, 8.5, 9.5, 11.9 and 15.9 degrees 2-theta±0.2 degrees 2-theta; an XRPD pattern as depicted in FIG. 17; and combinations of these data. Crystalline Form F1 of Valbenazine fumarate may be further characterized by the XRPD pattern having peaks at 4.7, 8.5, 9.5, 11.9 and 15.9 degrees 2-theta±0.2 degrees 2-theta, and also having one, two, three, four or five additional peaks selected from 14.5, 17.0, 18.5, 19.0 and 19.9 degrees 2-theta±0.2 degrees 2-theta.

Crystalline Form F1 of Valbenazine fumarate may be characterized by each of the above characteristics alone/or by all possible combinations, e.g. by XRPD pattern having peaks at 4.7, 8.5, 9.5, 11.9 and 15.9 degrees 2-theta±0.2 degrees 2-theta and an XRPD pattern as depicted in FIG. 17.

In another embodiment, the present disclosure further comprises a crystalline form of Valbenazine stearate designated as Form S1. The crystalline Form S1 of Valbenazine stearate can be characterized by data selected from one or more of the following: an XRPD pattern having peaks at 4.0, 6.0, 7.3, 10.0 and 14.1 degrees 2-theta±0.2 degrees 2-theta; an XRPD pattern as depicted in FIG. 18; and combinations of these data. Crystalline Form S1 of Valbenazine stearate may be further characterized by the XRPD pattern having peaks at 4.0, 6.0, 7.3, 10.0 and 14.1 degrees 2-theta±0.2 degrees 2-theta, and also having one, two, three, four or five additional peaks selected from 18.2, 20.2, 29.6, 32.6 and 36.8 degrees 2-theta±0.2 degrees 2-theta.

Crystalline Form S1 of Valbenazine stearate may be characterized by each of the above characteristics alone/or by all possible combinations, e.g. by XRPD pattern having peaks at 4.0, 6.0, 7.3, 10.0 and 14.1 degrees 2-theta±0.2 degrees 2-theta and an XRPD pattern as depicted in FIG. 18.

In yet another embodiment, the present disclosure further comprises a crystalline form of Valbenazine palmitate designated as Form P1. The crystalline Form P1 of Valbenazine palmitate can be characterized by data selected from one or more of the following: an XRPD pattern having peaks at 4.5, 6.7, 7.3, 11.3 and 15.8 degrees 2-theta±0.2 degrees 2-theta; an XRPD pattern as depicted in FIG. 19; and combinations of these data. Crystalline Form P1 of Valbenazine palmitate may be further characterized by the XRPD pattern having peaks at 4.5, 6.7, 7.3, 11.3 and 15.8 degrees 2-theta±0.2 degrees 2-theta, and also having one, two, three, four or five additional peaks selected from 20.9, 21.6, 22.6, 23.7 and 27.2 degrees 2-theta±0.2 degrees 2-theta.

Crystalline Form P1 of Valbenazine palmitate may be characterized by each of the above characteristics alone/or by all possible combinations, e.g. by XRPD pattern having peaks at 4.5, 6.7, 7.3, 11.3 and 15.8 degrees 2-theta±0.2 degrees 2-theta and an XRPD pattern as depicted in FIG. 19.

In a further embodiment, the present disclosure further comprises a crystalline form of Valbenazine sulfate designated as Form HS1. The crystalline Form HS1 of Valbenazine sulfate can be characterized by data selected from one or more of the following: an XRPD pattern having peaks at 6.8, 8.9, 12.6, 15.1 and 21.6 degrees 2-theta±0.2 degrees 2-theta; an XRPD pattern as depicted in FIG. 20; and combinations of these data. Crystalline Form HS1 of Valbenazine sulfate may be further characterized by the XRPD pattern having peaks at 6.8, 8.9, 12.6, 15.1 and 21.6 degrees 2-theta±0.2 degrees 2-theta, and also having one, two, three, four or five additional peaks selected from 17.8, 20.8, 22.9, 20.0 and 22.4 degrees 2-theta±0.2 degrees 2-theta.

Crystalline Form HS1 of Valbenazine sulfate may be characterized by each of the above characteristics alone/or by all possible combinations, e.g. by XRPD pattern having peaks at 6.8, 8.9, 12.6, 15.1 and 21.6 degrees 2-theta±0.2 degrees 2-theta and an XRPD pattern as depicted in FIG. 20.

In yet a further embodiment, the present disclosure further comprises a crystalline form of Valbenazine mesylate designated as Form MS1. The crystalline Form MS1 of Valbenazine mesylate can be characterized by data selected from one or more of the following: an XRPD pattern having peaks at 6.4, 10.3, 11.1, 12.8, and 13.7 degrees 2-theta±0.2 degrees 2-theta; an XRPD pattern as depicted in FIG. 21; and combinations of these data. Crystalline Form MS1 of Valbenazine mesylate may be further characterized by the XRPD pattern having peaks at 6.4, 10.3, 11.1, 12.8, and 13.7 degrees 2-theta±0.2 degrees 2-theta, and also having one, two, three, four or five additional peaks selected from 15.1, 16.9, 18.8, 23.1, and 24.5 degrees 2-theta±0.2 degrees 2-theta.

Crystalline Form MS1 of Valbenazine mesylate may be characterized by each of the above characteristics alone/or by all possible combinations, e.g. by XRPD pattern having peaks at 6.4, 10.3, 11.1, 12.8, and 13.7 degrees 2-theta±0.2 degrees 2-theta and an XRPD pattern as depicted in FIG. 21.

The present disclosure also provides the solid state form of Valbenazine or Valbenazine salt of the present disclosure for use in the preparation of other solid state forms of Valbenazine, Valbenazine salts and their solid state forms thereof.

The present disclosure further encompasses processes for preparing Valbenazine salt or solid state forms thereof. The process comprises preparing the solid state forms of the present disclosure, and converting it to Valbenazine salt. The conversion can be done, for example, by processes comprising reacting the obtained Valbenazine solid state form with an appropriate base to obtain the corresponding base-addition salt.

In another embodiment, the present disclosure encompasses the above described solid state forms of Valbenazine or Valbenazine salts for use in the preparation of pharmaceutical compositions and/or formulations, optionally for the treatment of central nervous system disorders, particularly involuntary hyperkinetic movement disorders such as drug-induced tardive dyskinesia and Tourette's syndrome.

In another embodiment, the present disclosure encompasses the use of the above described solid state forms of Valbenazine or Valbenazine salts for the preparation of pharmaceutical compositions and/or formulations. The present disclosure also provides the solid state forms of Valbenazine or Valbenazine salts of the present disclosure for use in the preparation of pharmaceutical compositions and/or formulations.

The present disclosure further provides pharmaceutical compositions comprising the solid state form of Valbenazine or Valbenazine salts according to the present disclosure.

In yet another embodiment, the present disclosure encompasses pharmaceutical formulations comprising the above described solid state form of Valbenazine or Valbenazine salts and at least one pharmaceutically acceptable excipient.

The present disclosure encompasses processes to prepare said formulations of Valbenazine or Valbenazine salts comprising combining the above solid state form of Valbenazine or Valbenazine salts and at least one pharmaceutically acceptable excipient.

The solid state forms of Valbenazine or Valbenazine salts as defined herein, as well as the pharmaceutical compositions or formulations thereof and at least can be used as medicaments, particularly for the treatment of central nervous system disorders, particularly involuntary hyperkinetic movement disorders such as drug-induced tardive dyskinesia and Tourette's syndrome.

The present disclosure also provides methods of treating central nervous system disorders, particularly involuntary hyperkinetic movement disorders such as drug-induced tardive dyskinesia and Tourette's syndrome, comprising administering a therapeutically effective amount of the solid state forms of Valbenazine or Valbenazine salts in the present disclosure, or at least one of the above pharmaceutical compositions or formulations, to a subject suffering from central nervous system disorders, particularly involuntary hyperkinetic movement disorders such as drug-induced tardive dyskinesia and Tourette's syndrome, or otherwise in need of the treatment.

The present disclosure also provides use of the solid state form of Valbenazine or Valbenazine salts of the present disclosure, or at least one of the above pharmaceutical compositions or formulations for the manufacture of a medicament for treating central nervous system disorders, particularly involuntary hyperkinetic movement disorders such as drug-induced tardive dyskinesia and Tourette's syndrome.

The present disclosure also provides processes for the preparation of Valbenazine or Valbenazine salts and intermediates in the preparation thereof.

Description of Method A—Chiral resolution of (±)-Tetrabenazine with (−)-DPTTA

The (R,R)- and (S,S)-enantiomers of racemic (±)-Tetrabenazine (Compound 1) can be efficiently separated by using (−)-Di-p-Toluoyl-Tartaric acid ((−)-DPTTA) as a resolving agent. Preferably 0.5-5 equivalents, or 0.6-3 equivalents, or 0.7-2.5 equivalents or 0.5-1 equivalent of the resolving agent may be used. Particularly, "equivalents" as used herein refers to, e.g. 0.5-5 moles of DPTTA per mole of racemic (±)-Tetrabenazine. Preferably the chiral resolution is carried out in a ketone or cyclic ketone, alcohol or ether, preferably wherein the solvent comprises a ketone, and more preferably wherein the solvent is acetone. Preferably, the solvent comprises a $C_3$-$C_7$-aliphatic ketone (preferably acetone, methyl ethyl ketone, or methylisobutyl ketone), a $C_{6-10}$ cyclic ketone (preferably cyclohexanone) or a $C_1$-$C_6$ alcohol (preferably methanol, ethanol, or isopropanol; or a $C_4$-$C_8$ aliphatic or cyclic ether (preferably THF, Me-THF or methyl tert-butyl ether); preferably wherein the solvent comprises a $C_3$-$C_7$-aliphatic ketone, and more preferably wherein the solvent is acetone. In particular, the reaction can be performed in polar solvents, preferably in ketones, preferably $C_3$-$C_7$-aliphatic ketones, preferably wherein the ketone is acetone, methyl ethyl ketone, MIBK (methylisobutyl ketone) or in $C_{6-10}$ cyclic ketones, preferably cyclohexanone; or in alcohols, preferably $C_1$-$C_6$ alcohols, more preferably Methanol, Ethanol, or Isopropanol; or in ethers, preferably $C_4$-$C_8$ aliphatic or cyclic ethers, more preferably THF, Me-THF, or MTBE. Particularly preferred solvent is acetone. The solvent can be used in 5-20 Volumes (v/wt), or 5-15 Volumes (v/wt), or 5-10 Volumes (v/wt) per weight of racemic (±)-Tetrabenazine. After precipitation, the isolated product is neutralized with an inorganic base such as $NH_4OH$, $K_2CO_3$, $Na_2CO_3$, or $NaHCO_3$ to obtain the desired (R,R)-enantiomer of Tetrabenazine ((+)-TBZ, Compound 2).

Compound 2 can be reduced by reducing agents, which favor the formation of (R,R,R)-Dihydrotetrabenazine ((R,R,R)-DHTBZ, Compound 3) rather than the formation of the (S,R,R)-Diastereomer of Dihydrotetrabenazine. Typical reducing agents which can be used are: $NaBH_4$, $BH_3$-complexes (particularly $BH_3$-THF complex) $NaBH(OAc)_3$, or $LiAlH_4$. The reaction can be conducted in alcoholic solvents, particularly in C1-C6 alcohols, preferably Methanol, Ethanol, or Isopropanol, or in ethers, preferably $C_4$-$C_8$ aliphatic or cyclic ethers, more preferably THF, Me-THF, or MTBE, or in other organic solvents such as Ethyl Acetate, or Toluene. The reaction is preferably performed at a range of temperatures from −30° C. to RT, preferably from −25° C. to +5° C., most preferably from −20° C. to −5° C.

Compound 3 can be reacted with an amine-protected Valine amino acid, i.e.:

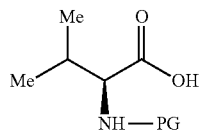

wherein PG is an amine protecting group, to obtain protected Valbenazine (PG-Valbenazine, Compound 4) using coupling reagents such as, but not limited to, DCC (N,N'-dicyclohexylcarbodiimide), EDC (1-Ethyl-3-(3-dimethylaminopropyl)carbodiimide) or DIC (N,N'-Diisopropylcarbodiimide), preferably with the addition of an appropriate additive such as, but not limited to, NHS (N-hydroxysuccinimide), HOBt (Hydroxybenzotriazole) or DMAP (4-Dimethylaminopyridine). The amino group of valine can be protected by protecting group PGs such as, but not limited to, Boc (tert-butyloxycarbonyl) or Cbz (carboxybenzyl) protecting groups. Any suitable protecting groups for amines can be used [e.g. see Greene's Protective Groups in Organic Synthesis, Fifth Edition (2014), P. G. M. Wuts, Wiley]. The reaction can be conducted in organic solvents such as, but not limited to, Me-THF, DCM, EtOAc or DMF in a range of temperatures from 0° C. to 100° C., preferably from 10° C. to 70° C., most preferably from 20° C. to 30° C.

Amino-protected Valbenazine (Compound 4) can be deprotected to obtain Valbenazine (Compound 5). This reaction may be performed using a suitable deprotecting agent in a suitable solvent depending on the nature of the protecting group itself [see Greene's Protective Groups in Organic Synthesis, Fifth Edition (2014), P. G. M. Wuts, Wiley]. Conversion of Compound 3 to Compound 5, or a salt thereof, can be performed without isolation of Compound 4. A further embodiment of the current invention is (+)-Tetrabenazine-(−)-DPTTA salt ((3R,11bR)-3-isobutyl-9,10-dimethoxy-2-oxo-1,2,3,4,5,6,7,11b-octahydropyrido[2,1-a]isoquinolin-5-ium (2 S,3S)-3-carboxy-2,3-bis((4-methylbenzoyl)oxy)propanoate). The invention further encompasses the use of (+)-Tetrabenazine-(−)-DPTTA salt or a crystalline form thereof for the preparation of an amino-protected Valbenazine (preferably wherein the amino-protecting group is Boc or Cbz), Valbenazine or a salt of Valbenazine, preferably Valbenazine di-tosylate, or for the preparation of (R,R)-Tetrabenazine, or (R,R,R)-Dihydrotetrabenazine.

Particularly, the present disclosure comprises Tetrabenazine-(−)-DPTTA salt in crystalline form. Preferably the crystalline form of (+)-Tetrabenazine-(−)-DPTTA salt is Form I. The crystalline Form I of (+)-Tetrabenazine-(−)-DPTTA salt can be characterized by data selected from one or more of the following: an XRPD pattern having peaks at 5.7, 7.1, 11.3, 17.7 and 19.1 degrees 2-theta±0.2 degrees 2-theta; an XRPD pattern as depicted in FIG. 27; and combinations of these data. Crystalline Form I of (+)-Tetrabenazine-(−)-DPTTA salt may be further characterized by the XRPD pattern having peaks at 5.7, 7.1, 11.3, 17.7 and 19.1 degrees 2-theta±0.2 degrees 2-theta, and also having one, two, three, four or five additional peaks selected from 16.5, 17.0, 20.7, 22.4 and 23.9 degrees 2-theta±0.2 degrees 2-theta.

The solid state form of (+)-Tetrabenazine-(−)-DPTTA salt according to the present disclosure may have advantageous properties selected from at least one of: chemical, enantiomeric/isomeric, or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

Description of Method B—Asymmetric Transfer Hydrogenation (ATH) of Tetrabenazine In a further aspect, the present disclosure provides a process to obtain (2R,3R,11bR)-Dihydrotetrabenazine (Compound 3) by an asymmetric transfer hydrogenation (ATH) of the racemic mixture of (R,R)- and (S,S)-Tetrabenazine using an ATH chiral metal catalyst such as a chiral Ru(II), Rh(II), Ir(II), or Fe(II) catalyst, preferably a Ru(II)-Noyori catalyst, more preferably a Ru(II)-DPEN catalyst (for example RuCl(p-cymene)[(R,R)-Ts-DPEN]).

The asymmetric hydrogenation of racemic Tetrabenazine yields a diastereomeric mixture of (2R,3R,11bR)-Dihydrotetrabenazine (Compound 3), originating from the (3R,11bR)-enantiomer of Tetrabenazine, and (2R,3S,11bS)-Dihydrotetrabenazine, originating from the (3S,11bS)-enantiomer of Tetrabenazine. This diastereomeric mixture can be further separated to obtain (R,R,R)-Dihydrotetrabenazine, which is a much easier task than separating a racemic mixture such as (R,R)- and (S,S)-Tetrabenazine (Compound 1) due to the different physical properties of a diastereomeric pair in comparison to a racemic pair. This allows separation using conventional methods such as crystallization or chromatography.

The reaction is preferably conducted using from 0.01-1 mole %, preferably 0.1 to 0.8 mole %, most preferably 0.4-0.6 mole % of ATH chiral catalyst relative to the racemic tetrabenazine starting material. Preferably the chiral catalyst is a Ru(II) asymmetric catalyst, typically a Ru(II)-Cl(arene)(diamine) or $Ru(II)Cl_2(PAr_2)_2$(diamine) catalyst, in the presence of a hydrogen donor such as $H_2$, $HCO_2H$ or Isopropanol The reaction also employs a base. In particular the reaction employs an amine base such as $Et_3N$ (triethylamine), DABCO (1,4-Diazabicyclo[2.2.2]octane), or DBU (1,8-Diazabicyclo(5.4.0)undec-7-ene) or an alkali metal base such as KOH, KO$^t$Bu, or KO$^i$Pr. The reaction is preferably conducted in a suitable solvent. Suitable solvents may be aprotic solvents such as THF, DMF, or DMSO, or aromatic solvents such as Chlorobenzene, Toluene, or Benzene. The reaction is preferably carried out at a temperature between 0° C.-100° C., preferably between 20-80° C., most preferably between 30-60° C.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods

X-Ray Powder Diffraction Method (XRPD):

XRPD analysis was performed on ARL (SCINTAG) powder X-Ray diffractometer model X'TRA equipped with a solid state detector. Copper radiation of 1.5418 Å was used. Scanning parameters: range: 2-40 degrees two-theta; scan mode: continuous scan; step size: 0.05°, and a rate of 3 deg/min.

Prior to analysis, the samples were gently ground using a mortar and pestle to obtain a fine powder. Optionally, silicon powder can be added in a suitable amount as internal standard in order to calibrate the positions of the diffractions. The ground sample was adjusted into a cavity of the sample holder and the surface of the sample was smoothed using a cover glass.

Thermogravimetric Analysis (TGA)

Heating between 25-250° C., heating rate: 10° C./min.
Sample weight: 7-15 mg.
Crucible: 150 µL alumina crucible.
Purging with 40 ml/min N$_2$ flow.

FT-IR Spectroscopy

Thermo FT-IR Spectrometer Nicolet.
The samples were studied in ATR mode.
The spectrum was scanned between 4000-400 cm$^{-1}$.
All the spectra were measured in 16 scans.
Resolution: 4.0 cm$^{-1}$.

$^{13}$C Solid-State NMR Method $^{13}$C SSNMR was performed at 125 MHz using Bruker Avance II+ 500
SB probe using 4 mm rotors
Magic angle was set using KBr
Homogeneity of magnetic field checked using adamantane
Parameters for Cross polarization optimized using glycine
Spectral reference set according to glycine as external standard (176.03 ppm for low field carboxyl signal)
Scanning parameters:
Magic Angle Spinning Rate: 11 kHz; Delay time: 3 sec.;
Number of Scans: 2048 scans;
Temperature: 0° C.

EXAMPLES

Valbenazine starting material can be prepared according to methods known from the literature (for example U.S. Pat. No. 8,039,627).

(±)-Tetrabenazine is the active pharmaceutical ingredient of the approved drug XENAZINE and is commercially available as a racemic mixture of (3R,11bR)-Tetrabenazine and (3S,11bS)-Tetrabenazine.

P-toluenesulfonic acid was purchased from Sigma Aldrich as monohydrate salt.

Example 1 Preparation of Valbenazine Form L1

Valbenazine was charged in glass vial with magnetic stir (36 mg) and dimethylacetamide (20 µL, 1.8 vol). The obtained slurry was heated to 70° C. and clear solution was obtained. Water (215 µL, 6 vol) was added and precipitation was observed. The obtained slurry was stirred for 2 hours. The slurry was filtrated and characterized by X-ray powder diffractogram to give Valbenazine form L1 as depicted in FIG. 1.

Example 2: Preparation of Valbenazine Form L2

Valbenazine (66 mg) and a mixture of 9.5:0.5 dichloromethane/methanol (3.2 ml, 48.5 vol) were charged in glass vial. The obtained clear solution was evaporated to give solid that was dissolved again in 9.5:0.5 dichloromethane/methanol (1.6 ml, 24 vol). The solution was evaporated to give oil that crystallized to give a solid that characterized by X-ray powder diffractogram to give Valbenazine form L2 as depicted in FIG. 2.

Example 3: Preparation of Valbenazine Form L3

Valbenazine was charged in flask (4 g) and dichloromethane was added (100 ml, 25 vol) clear solution was obtained. After a few minutes precipitation was observed. The crystals were filtrated and characterized by X-ray powder diffractogram to give Valbenazine form L3 as depicted in FIG. 3.

Example 4: Preparation of Valbenazine Form L4

1 g of Valbenazine was charged in flask. Methanol was added (25 ml, 25 vol) and clear solution was obtained. The solution was evaporated. The obtained solid was characterized by X-ray powder diffractogram to give Valbenazine form L4 as depicted in FIG. 4.

Example 5: Preparation of Valbenazine Form L2

Valbenazine (126 mg) was charged in a vial and was heated to 100° C. to melt. The molten substance, was stored in 100% RH humidity chamber at room temperature over night to give crystals that were vacuum-dried and characterized by X-ray powder diffractogram to give Valbenazine form L2 as depicted in FIG. 5.

Example 6: Preparation of Valbenazine Tosylate Form T1

Valbenazine (98 mg) was dissolved in methyl ethyl ketone (1 ml). P-toluenesulfonic acid (88 mg, 1.86 eq.) was then added and mixed until clear solution was obtained. After a few minutes precipitation was observed and filtrated. The crystals were vacuum-dried and characterized by X-ray powder diffractogram to give Valbenazine tosylate form T1.

Example 7: Preparation of Valbenazine Tosylate Form T1

Valbenazine (101 mg) was slurried in water (1 ml). P-toluenesulfonic acid (105 mg, 2.25 eq.) was then added and mixed until clear solution was obtained. The solution was stirred overnight precipitation was observed and filtrated. The crystals were vacuum-dried and characterized by X-ray powder diffractogram to give Valbenazine tosylate form T1.

Example 8: Preparation of Valbenazine Tosylate Form T2

Valbenazine (112 mg) was dissolved in 1-propanol (1 ml). P-toluenesulfonic acid (119 mg, 2.2 eq.) was then added and mixed until clear solution was obtained. The solution was stirred overnight, precipitation was observed and filtration was done. The crystals were vacuum-dried and characterized by X-ray powder diffractogram to give Valbenazine tosylate form T2 as depicted in FIG. 7.

Example 9: Preparation of Valbenazine Tosylate Form T2

Valbenazine (116 mg) was dissolved in Ethanol (1 ml). P-toluenesulfonic acid (114 mg, 2.1 eq.) was then added and mixed until clear solution was obtained. The solution was stirred overnight, precipitation was observed and filtration was done. The crystals were vacuum-dried and characterized by X-ray powder diffractogram to give Valbenazine tosylate form T2.

Example 10: Preparation of Valbenazine Tosylate Form T2

Valbenazine (246 mg) was dissolved in methyl ethyl ketone (2.46 ml). P-toluenesulfonic acid (240 mg, 2.1 eq.) was then added and mixed until clear solution was obtained. After a few minutes, precipitation was observed and filtration was done. The crystals were vacuum-dried and characterized by X-ray powder diffractogram to give Valbenazine tosylate form T2.

Example 11: Preparation of Valbenazine Tosylate Form T2

Valbenazine (363 mg) was dissolved in Cyclopentyl methyl ether (3.36 ml). P-toluenesulfonic acid (366 mg, 2.1 eq.) was then added and mixed until clear solution was obtained. The solution was stirred overnight, precipitation was observed and filtration was done. The crystals were vacuum-dried and characterized by X-ray powder diffractogram to give Valbenazine tosylate form T2.

Example 12: Preparation of Valbenazine Tosylate Form T3

Valbenazine (335 mg) was dissolved in 1,4-dioxane (3.36 ml). P-toluenesulfonic acid (312 mg, 2.0 eq.) was then added and mixed until clear solution was obtained. The solution was stirred over the weekend, precipitation was observed and filtration was done. The crystals were vacuum-dried and characterized by X-ray powder diffractogram to give Valbenazine tosylate form T3 as depicted in FIG. 8.

Example 13: Preparation of Valbenazine Tosylate Form T3

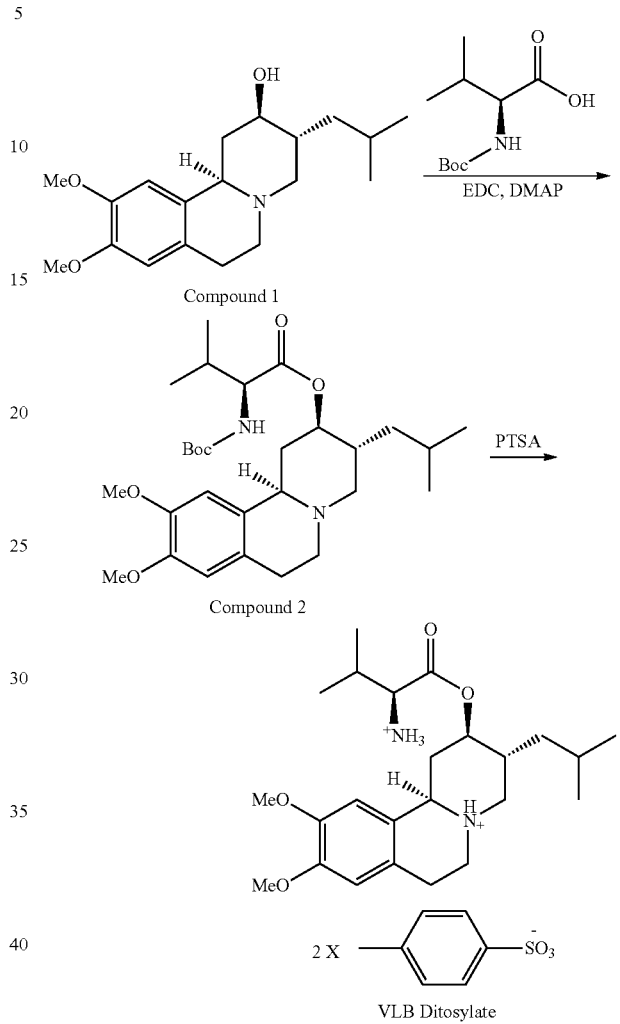

(2R,3R,11bR)-3-isobutyl-9,10-dimethoxy-1,3,4,6,7,11b-hexahydro-2H-pyrido[2,1-a]isoquinolin-2-ol (10 gr, 0.03 mol, 1 eq) was dissolved in 100 ml of Me-THF (10 V vs. Compound 1 v/w). Then Boc-Val-OH was added (10.21 gr, 0.047 mol, 1.5 eq) followed by the addition of 4-(dimethylamino)pyridine (DMAP) (1.91 gr, 0.015 mol, 0.5 eq). Finally, N-(3-dimethylaminopropyl)-N'-ethylcarbodiimide hydrochloride (EDC-HCl) was added (13.21 gr, 0.068 mol, 2.2 eq) and the reaction mixture was stirred at RT for 2.5 hours. Upon completion, 100 ml of water was added to the reaction mixture (10 V vs. Compound 1 v/w). The phases were separated. The organic phase was washed with Water (10V). The aqueous phase was removed. Then p-toluenesulfonic acid (PTSA) was added (41.71 gr, 0.21 mol, 7 eq). The reaction mixture was stirred at RT for 16 hours. Upon completion, the precipitated product was filtered and washed twice with 10 ml of Me-THF (2×1 V vs. Compound 1 v/w). The obtained product—Valbenazine tosylate was then dried in a vacuum oven at 35° C. for 3 days to obtain 11.33 gr of the desired product (47% yield over two steps, 99.58% purity). The crystalline form of the product was found to be form T3 according to XRPD.

Example 14: Preparation of Amorphous Valbenazine Tosylate

Valbenazine tosylate form T2 (3 g) was dissolved in 200 ml of dichloromethane:methanol (1:1 v/v) mixture. A clear solution was obtained and the solution was evaporated at vacuum to give amorphous Valbenazine tosylate.

Example 15: Preparation of Valbenazine Tosylate Form T3

Amorphous Valbenazine tosylate (50 mg) was suspended in tetrahydrofuran (140 μL, 3 Vol) and stirred at 0° C. overnight. The crystals were vacuum-dried and characterized by X-ray powder diffraction to give Valbenazine tosylate form T3.

Example 16: Preparation of Valbenazine Tosylate Form T3

Amorphous Valbenazine tosylate (50 mg) was suspended in methyl ethyl ketone (140 μL, 3 Vol) and stirred at 0° C. overnight. The crystals were vacuum-dried and characterized by X-ray powder diffraction to give Valbenazine tosylate form T3.

Example 17: Preparation of Valbenazine Tosylate Form T3

Amorphous Valbenazine tosylate (50 mg) was suspended in 1,4 Dioxane (140 μL, 3 Vol) and stirred at 0° C. overnight. The crystals were vacuum- and characterized by X-ray powder diffraction to give Valbenazine tosylate form T3.

Example 18: Preparation of Valbenazine Tosylate Form T4

Valbenazine (100 mg) and p-toluenesulfonic acid (118 mg, 2.57 eq.) were melted at 100° C.; 1.6 ml of water was added to give clear solution. The solution was cooled at a rate of 5° C./min; after 1 h there was precipitation. The slurry was filtrated and the crystals were vacuum-dried and characterized by X-ray powder diffractogram to give Valbenazine tosylate form T4 as depicted in FIG. 9.

Example 19: Preparation of Valbenazine Tosylate Form T4

A 250 ml reactor was charged with Valbenazine (2.5 g) and p-toluenesulfonic acid (2.87 g, 2.50 eq.) in 20 ml of water. The mixture was heated to 100° C. to give a clear solution. The solution was cooled to 0° C. during 2 h. The crystals were filtered and characterized by X-ray powder diffractogram to give Valbenazine tosylate form T4.

Example 20: Preparation of Valbenazine Tosylate Form T5

Valbenazine tosylate form T4 (1.5 mg) was dried in a lyophilizer under the conditions of 50° C. and vacuum of 30 μbar for 27 hours. The sample was characterized by X-ray powder diffractogram to give Valbenazine tosylate form T5 as depicted in FIG. 10.

Example 21: Preparation of Valbenazine Tosylate Form T6

Valbenazine tosylate form T4 (60 mg) was charged in a vial with a magnetic stirrer. THF (36 vol, 2.1 ml) was added and the obtained slurry was stirred at room temperature overnight. The slurry was filtrated and characterized by X-ray powder diffractogram to give Valbenazine tosylate form T6 as depicted in FIG. 11.

Example 22: Preparation of Valbenazine Tosylate Form T7

Valbenazine tosylate form T3 (96 mg) was charged in a vial with a magnetic stirrer. Isobutanol (10.42 vol, 2.1 ml) was added and the obtained slurry was stirred at room temperature overnight. The slurry was filtrated and characterized by X-ray powder diffractogram to give Valbenazine tosylate form T7 as depicted in FIG. 12.

Example 23: Preparation of Valbenazine Tosylate Form T8

Amorphous Valbenazine tosylate (202 mg) was charged in a vial with a magnetic stirrer. 1,4 Dioxane (3 vol, 0.8 ml) was added and the obtained slurry was stirred at 0° C. for 3 h. The slurry was filtrated and characterized by X-ray powder diffraction to give Valbenazine tosylate form T8 as depicted in FIG. 13.

Example 24: Preparation of Valbenazine Tosylate Form T9

Valbenazine tosylate form T6 (2 gr) was dried without freezing in a lyophilizer at between 30° C. to 50° C. and less than 100 μbar for 55 hours. The product was characterized by X-ray powder to give Valbenazine tosylate form T9 as depicted in FIG. 14.

Example 25: Preparation of Valbenazine Tosylate Form T10

Valbenazine tosylate form T9 as prepared according to example 24 was left in a vial for 3 days at RT without stirring to give a mixture of T9+T10 the mixture was dried without freezing in a lyophilizer at 50° C. and less than 100 μbar, total time of drying was 22 h. The product was characterized by X-ray powder to give Valbenazine tosylate form T10 as depicted FIG. 15.

Example 26: Preparation of Valbenazine Tosylate Form T10

Valbenazine tosylate form T6 (THF solvate, 0.2 gr) was heated in a vacuum oven for 1 hour, at about 70° C. The solid was tested by XRD, and found to be Valbenazine tosylate Form T10.

Example 27: Preparation of Valbenazine Tosylate Form T12

(2R,3R,11bR)-3-isobutyl-9,10-dimethoxy-1,3,4,6,7,11b-hexahydro-2H pyrido[2,1-a]isoquinolin-2-ol (43.6 gr, 136 mmol) was slurried in 1 Vol. di-chloromethane (DCM, 43.6 mL) and charged into a 1 L reactor. 4-(dimethylamino)-pyridine (DMAP, 8.3 g, 68 mmol), Boc-Val-OH (44.5 gr, 204 mmol) and 5 Vol. (218 mL) of DCM were added to the reactor and stirred for 5 min at room temperature. Then N-(3-dimethylaminopropyl)-N'-ethylcarbodiimide HCl (EDC.HCl, 57.6 gr, 300 mmol) was added to the reaction mixture followed by addition of 1 Vol (43.6 mL) of DCM. The mixture was stirred for 3 hours at room temperature.

After completion of reaction, the reaction mixture was washed with water (10 Vol.) followed by phase separation. Additional washing with water (10 vol) was carried out and after phase separation p-Toluenesulfonic acid monohydrate (104 g, 544 mmol) was added to the organic phase and stirred for 19 hours at 35° C. 87 ml of the obtained solution was diluted with additional DCM (13 ml) and MeOH (100 ml). The solvents were evaporated to obtain an oil. THF (100 ml) was then added to the oil and evaporated. The obtained oil was dissolved in THF:MeOH (98:2, 5.6 vol) and the solution was cooled to −5° C. The solution was then seeded with Valbenazine tosylate form T6 and stirred for 18 hours at −5° C. The precipitate was collected by vacuum filtration and dried in a vacuum oven at 70° C. (less than 50 mbar) for 72 hours. The hot solid was taken out from the oven directly to room temperature under nitrogen environment to produce Valbenazine tosylate form T12. Form T12 was characterized by X-ray powder and its diffractogram is presented in FIG. 16.

Example 28: Preparation of Seeding Crystals Valbenazine Tosylate Form T6

Amorphous form of Valbenazine tosylate (241 mg) was slurried in THF/MeOH (0.2% MeOH, 5.01 ml, 20 vol) at 0° C. for 24 hours. The product was isolated by vacuum filtration to afford Valbenazine tosylate Form T6.

Example 29: Preparation of Valbenazine Tosylate Mixture of Form T10 and Form T12

Valbenazine tosylate form T10 (100 mg) was heated to 100° C. in an oven for 1 hour. The hot solid was taken out from the oven directly to a sealed vial at room temperature for 24 hrs. The solid was characterized by X-ray powder diffractogram to give a mixture of valbenazine tosylate form T10 and form T12. The diffractogram is presented in FIG. 22.

Example 30: Preparation of Valbenazine Tosylate Form T10

501 mg of amorphous valbenazine tosylate was slurried in 5 mL (10 Vol.) of iso-butanol, cooled to 0° C. and stirred overnight. The slurry was filtered, the resulting solid was dried under vacuum at 70° C. overnight. The white powder was further dried under vacuum at 100° C. overnight to afford Valbenazine tosylate form T10.

Example 31: Preparation of Valbenazine Tosylate Form T10

501 mg of amorphous valbenazine tosylate was slurried in 5 ml (10 Vol.) of dioxane, cooled to 0° C. and stirred over 48 h. The slurry was filtered and dried under vacuum at 70° C. overnight to afford Valbenazine tosylate form T10.

Example 32: Preparation of Valbenazine Tosylate Form T7

(2R,3R,11bR)-3-isobutyl-9,10-dimethoxy-1,3,4,6,7,11b-hexahydro-2H pyrido[2,1-a]isoquinolin-2-ol (21.8 gr, 68 mmol) was dissolved in 1 Vol. (21.8 mL) DCM and charged into the reactor. DMAP (4.15 gr, 34 mmol), Boc-Val-OH (22 gr, 102 mmol) and 7 Vol. (152.6 mL) DCM were added. The mixture was stirred at RT until complete dissolution. EDC.HCl (28.8 gr, 150 mmol) in 2 Vol. of DCM was added. The mixture was stirred over 3 hours at 25° C. followed by washings with H$_2$O (10 Vol.×2). p-Toluenesulfonic acid monohydrate (52 gr, 272 mmol) was added to the washed mixture and stirred overnight at 35° C. Iso-butanol 5 Vol. (109 mL) was added and followed by distillation at 35° C. (under vacuum conditions) to 5 Vol. of the mixture. The mixture was cooled to 15° C., followed by seeding with 1% (w/w) of form T7 of Valbenazine tosylate and cooling to 5° C. over 1 h. After cooling, 2 Vol. (44 mL) of isobutanol were added followed by stirring overnight. The precipitate was filtered and washed with 2 Vol. (21.8 mL) of isobutanol. A white powder was obtained (73.55% yield) to afford Valbenazine tosylate form T7.

Example 33: Preparation of Valbenazine Fumarate Form F1

A flask was charged with Valbenazine (500 mg) and acetone (2.5 ml, 5 vol) and stirred at RT until a clear solution was obtained. Fumaric acid (278 mg, 2 eq.) was added and the mixture was stirred overnight at RT. A thick precipitation was obtained and another 5 ml of acetone were added. The slurry was filtered and the residue characterized by X-ray powder diffractogram to give Valbenazine fumarate Form F1 as depicted in FIG. 17.

Example 34: Preparation of Valbenazine Stearate Form S1

A flask was charged with Valbenazine (500 mg) and 2-Methyltetrahydrofuran (Me-THF) (2.5 ml, 5 vol) and stirred at RT until a clear solution was obtained. Stearic acid (856 mg, 2.5 eq.) was added and the mixture was stirred overnight at RT. The flask was transferred to an ice bath and the solution was cooled for 15 min with stirring to give a precipitation. The crystals were filtered and characterized by X-ray powder diffractogram to give Valbenazine stearate Form S1 as depicted in FIG. 18.

Example 35: Preparation of Valbenazine Palmitate Form P1

A flask was charged with Valbenazine (50 mg) and Acetone (500 µL, 5 vol) and stirred at RT until a clear solution was obtained. Palmitic acid (153 mg, 2.5 eq.) was added and the mixture was stirred overnight. The crystals were filtered and characterized by X-ray powder diffractogram to give Valbenazine palmitate Form P1 as depicted in FIG. 19.

Example 36: Preparation of Valbenazine Sulfate Form HS1

A flask was charged with Valbenazine (50 mg) and n-butanol (500 µL, 5 vol) and stirred at RT until a clear solution was obtained. Sulfuric acid (16 µL, 2.5 eq.) was added and the mixture was stirred for 3 h at RT. The crystals were filtered and characterized by X-ray powder diffractogram to give Valbenazine sulfate Form HS1 as depicted in FIG. 20.

Example 37: Preparation of Valbenazine Mesylate Form MS1

To a stirred solution of Valbenazine base (2 g, 1 eq) in a mixture of Isopropanol (20 ml, 10 vol) and diethyl ether (6.5 ml, 3.25 vol), methanesulfonic acid (651 µL, 2.10 eq) was added and clear solution was obtained. The solution was stirred at RT for 30 minutes. The solution was cooled in an ice bath for 2 h and an oil was obtained. The mixture was stirred at RT overnight. The solid was filtered under nitrogen, washed with 4 ml diethyl ether and dried in a vacuum oven at 50° C. overnight to give Valbenazine mesylate Form MS1. The product was characterized by XRPD as depicted in FIG. 21.

Example 38: Chiral Resolution of Tetrabenazine with (−)-DPTTA (Method A)

Scheme 2: Chiral resolution of (±)-Tetrabenazine with (−)-DPTTA

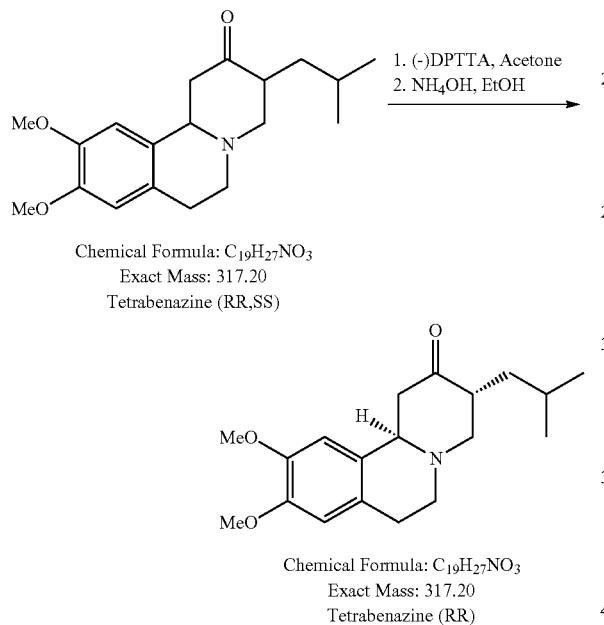

(±)-Tetrabenazine (Compound 1, 200 gr, 0.62 mol, 1 eq) was dissolved in 2 L of Acetone (10 V vs. Tetrabenazine v/wt) in a 3 L glass reactor. Then (−)-O,O'-Di-p-toluoyl-L-tartaric acid ((−)-DPTTA) was added (243.6 gr, 0.62 mol, 1 eq). The reaction mixture was stirred at RT for 16 h. The precipitated product was filtrated and washed with Acetone (2×0.5 V vs. Tetrabenazine v/wt). The mother liquor after precipitation was distilled off. The obtained residue was dissolved in 1 L of Acetone (5 V vs. Tetrabenazine v/wt) in a 3 L reactor, heated to 60° C. and stirred for 2 hours. The solution was then cooled to RT and stirred for 16 h. The precipitated product was filtrated and washed with Acetone (2×0.5 V vs. Tetrabenazine v/wt). The precipitated product-(+)-Tetrabenazine-(−)-DPTTA salt from both steps was combined and dissolved in EtOH (6 V vs. (+)Tetrabenazine-(−)-DPTTA salt v/wt) in a 3 L glass reactor and cooled to 0° C. The pH was adjusted to pH=8-8.5 with NH4OH. Water (10V vs. (+)-Tetrabenazine-(−)-DPTTA salt v/wt) was added dropwise and the reaction mixture was stirred at 0° C. for 1 h. The precipitated product was filtrated and washed with water (2 V, vs. (+)-Tetrabenazine-(−)-DPTTA salt v/wt) to obtain the desired (+)-Tetrabenazine (R,R) enantiomer (Compound 2, 134 gr, 67% overall yield, 97-98% chiral purity).

Example 39: Asymmetric Transfer Hydrogenation of (±)-Tetrabenazine (Method B)

Scheme 3: Asymmetric transfer hydrogenation of (±)-Tetrabenazine

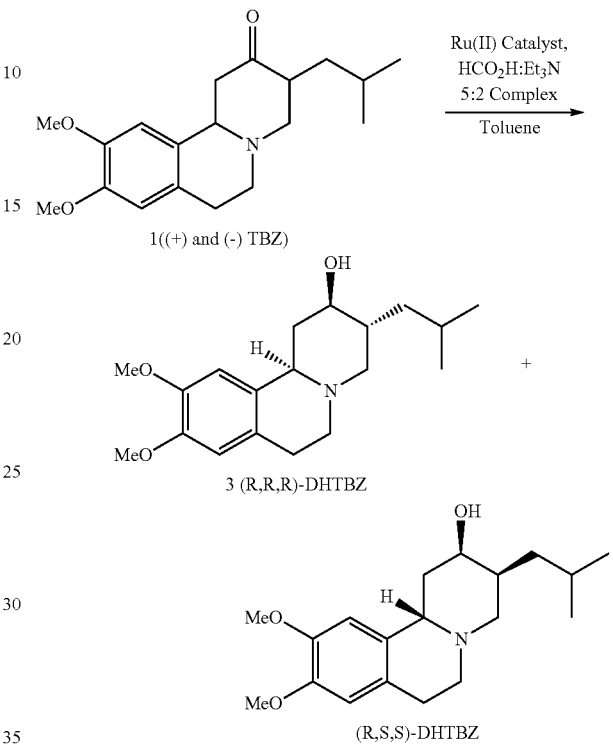

(±)-Tetrabenazine (Compound 1, 3 gr, 0.0095 mol, 1 eq) was dissolved in 18 ml of Toluene (6 V vs. Tetrabenazine v/wt) in a 100 ml round-bottom flask under Nitrogen atmosphere. RuCl(p-cymene)[(R,R)-Ts-DPEN] was added (0.03 gr, 0.0005 mol, 0.005 eq), followed by the addition of 5:2 HCO$_2$H:Et$_3$N complex (4.37 ml, 0.05 mol, 5.4 eq). The reaction mixture was heated to 50° C. and stirred for 16 h. Upon completion, the reaction mixture was diluted with 50 ml of water and 50 ml of Ethyl Acetate. The layers were separated and the organic layer was washed with 50 ml of water. The organic layer was then dried with Na$_2$SO$_4$, filtered and the solvent was removed under reduced pressure to obtain (R,R,R)-Dihydrotetrabenazine (Compound 3) and its diastereomer—(R,S,S)-Dihydrotetrabenazine as a 1:1 mixture.

Example 40: Preparation of (+)-Tetrabenazine ((3R, 11bR)-3-isobutyl-9,10-dimethoxy-1,3,4,6,7,11b-hexahydro-2H-pyrido[2,1-a]isoquinolin-2-one)

A: (3R,11bR)-3-isobutyl-9,10-dimethoxy-1,3,4,6,7,11b-hexahydro-2H-pyrido[2,1-a]isoquinolin-2-one, (−)-Di-p-toluoyl-L-tartrate (−)-Di-p-toluoyl-L-tartaric acid (730.3 g, 1.89 mole), 3-isobutyl-9,10-dimethoxy-1,3,4,6,7,11b-hexahydro-2H-pyrido[2,1-a]isoquinolin-2-one (600 g, 1.89 mole) and Acetone (6000 ml, 10 vol) were charged in to reactor vessel at −10° C. The obtained solution was stirred at −5° C. till precipitations were obtained. The reaction mixture was then heated to 25° C. and stirred for 10 hours. The slurry was heated to reflux and stirred for 2 hours at reflux temperature. The obtained slurry was cooled to 25° C. and stirred for additional 12 hours. The product was isolated by vacuum filtration, washed with Acetone and dried in vacuum oven at 40° C. to obtain (3R,11bR)-3-isobutyl-9,10-dimethoxy-1,3, 4,6,7,11b-hexahydro-2H-pyrido[2,1-a]isoquinolin-2-one, (−)-Di-p-toluoyl-L-tartarate (771 g, 93.3% chiral purity; 58% yield).

Mother liquor from the previous step was loaded to the reactor vessel; the volume of the solution was reduced by distillation to total volume of 2 liters. The solution was seeded with (3R,11bR)-3-isobutyl-9,10-dimethoxy-1,3,4,6, 7,11b-hexahydro-2H-pyrido[2,1-a]isoquinolin-2-one, (−)-Di-p-toluoyl-L-tartarate (0.44 gr) at 25° C. and stirred for 5 hours. The obtained slurry was heated to 62° C., stirred for 2 hours then cooled to 25° C. for 2 hours and stirred at that temperature for 18 hours. The product was isolated by vacuum filtration washed with Acetone (2*0.5 vol) and dried in vacuum oven at 40° C. for 16 hours to obtain (3R,11bR)-3-isobutyl-9,10-dimethoxy-1,3,4,6,7,11b-hexahydro-2H-pyrido[2,1-a]isoquinolin-2-one, (−)-Di-p-toluoyl-L-tartarate (265 g, 20% yield).

B: (3R,11bR)-3-isobutyl-9,10-dimethoxy-1,3,4,6,7, 11b-hexahydro-2H-pyrido[2,1-a]isoquinolin-2-one (3R,11bR)-3-isobutyl-9,10-dimethoxy-1,3,4,6,7,11b-hexahydro-2H-pyrido[2,1-a]isoquinolin-2-one, (−)-Di-p-toluoyl-L-tartarate (1031 g, 1.466 mole), Ethanol (6186 ml, 6 vol) and water (1031 ml, 1 vol) were charged to reactor vessel, cooled to 0° C. then NaHCO$_3$ (309.3 g, 3.66 mole) and additional amount of water (3093 ml, 3 vol) were added to the reaction mixture and stirred for 2 hour. Additional water (6186 ml, 6 vol) was added dropwise and stirred for 15 hours. The product (3R,11bR)-3-isobutyl-9,10-dimethoxy-1,3,4,6,7,11b-hexahydro-2H-pyrido[2,1-a]isoquinolin-2-one was isolated by vacuum filtration, washed with water and dried in vacuum oven (422 g, 90.75% yield, 98.42% chiral purity).

Example 41: Preparation of (R,R,R)-DHTBZ ((2R, 3R,11bR)-3-isobutyl-9,10-dimethoxy-1,3,4,6,7,11b-hexahydro-2H-pyrido[2,1-a]isoquinolin-2-ol)-

(3R,11bR)-3-isobutyl-9,10-dimethoxy-1,3,4,6,7,11b-hexahydro-2H-pyrido[2,1-a]isoquinolin-2-one (376 g, 0.945 mole) and THF (3760 ml, 10 vol), were loaded to the reactor and cooled to −15° C. BH3*THF 1 M solution (1743.6 ml, 1.74 eq) was added dropwise during 5.5 hours. The reaction mixture was stirred for 2 hours and the reaction completion was monitored by HPLC. Ammonium hydroxide solution (25%, 4512 ml, 12 vol) was added dropwise during 3 hours. The solution was heated to 35° C. and stirred for 12 hours. The solution was cooled to 25° C., NaCl sat. Solution (1880 ml, 5 vol) and MTBE (1880 ml, 5 vol) were added. The organic phase was evaporated to reduce the volume to 400-450 ml and then EtOH (1880 ml, 5 vol) was added. The product was precipitated by dropwise addition of water (3760 ml, 10 vol) during 1.5 hours and stirred for 16 hours. The product was collected by vacuum filtration, washed with EtOH/Water 1:4 (940 ml, 2.5 vol) and dried in vacuum oven at 35° C. for 48 hours to obtain (302 g, 80.4% yield, 96.3% purity).

The invention claimed is:

1. A process for the chiral resolution of (±)-Tetrabenazine comprising combining (±)-Tetrabenazine with (−)-O,O'-Di-p-Toluoyl-L-Tartaric acid ((−)-DPTTA) to form (+)-Tetrabenazine-(−)-DPTTA salt.

2. The process according to claim 1 further comprising converting the (+)-Tetrabenazine-(−)-DPTTA salt to (R,R)-Tetrabenazine, (R,R,R)-Dihydrotetrabenazine, or Valbenazine or a salt thereof.

3. A process for the preparation of (R,R,R)-Dihydrotetrabenazine comprising chiral resolution of (±)-Tetrabenazine using (−)-O,O'-Di-p-Toluoyl-L-Tartaric acid ((−)-DPTTA) as resolving agent.

4. The process according to claim 3, wherein the chiral resolution of (±)-Tetrabenazine comprises combining (±)-Tetrabenazine with (−)-O,O'-Di-p-Toluoyl-L-Tartaric acid ((−)-DPTTA) in a solvent to form (+)-Tetrabenazine-(−)-DPTTA salt.

5. The process according to claim 4, wherein the solvent comprises a ketone, cyclic ketone, alcohol, ether, or acetone.

6. The process according to claim 5, wherein the solvent comprises a $C_3$-$C_7$ aliphatic ketone, a $C_{6-10}$ cyclic ketone, a $C_1$-$C_6$ alcohol, a $C_4$-$C_8$ aliphatic or cyclic ether, or acetone.

7. The process according to claim 1, wherein the (+)-Tetrabenazine-(−)-DPTTA salt is converted to (R,R)-Tetrabenazine by treatment with a base.

8. The process according to claim 7, wherein the (R,R)-Tetrabenazine is further converted to (R,R,R)-Dihydrotetrabenazine by treatment with a reducing agent.

9. The process according to claim 8 wherein the (R,R,R)-Dihydrotetrabenazine is converted to Valbenazine or a salt thereof.

10. The process according to claim 9, wherein (R,R,R)-Dihydrotetrabenazine is reacted with an amino-protected Valine to obtain an amino-protected Valbenazine:

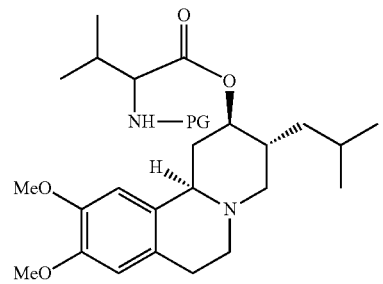

wherein PG is Boc or Cbz.

11. The process according to claim 10, wherein the amino-protected Valbenazine is converted to Valbenazine or a salt thereof.

12. The process according to claim 11, wherein the amino-protected Valbenazine is Boc- or Cbz-protected Valbenazine, which is converted to Valbenazine di-tosylate, by reaction with p-toluenesulfonic acid.

13. A process according to claim 1, wherein (+)-Tetrabenazine-(−)-DPTTA salt is isolated.

14. The process according to claim 13, wherein the (+)-Tetrabenazine-(−)-DPTTA salt is crystalline.

15. The process according to claim 14, wherein the (+)-Tetrabenazine-(−)-DPTTA salt is characterized by data selected from one or more of the following:
  (i) an MOD having peaks at 5.7, 7.1, 11.3, 17.7 and 19.1 degrees 2-theta±0.2 degrees 2-theta; and/or
  (ii) an XRPD pattern as depicted in FIG. 27.

16. The crystalline form of (+)-Tetrabenazine-(−)-DPTTA salt according to claim 15 characterized by an XRPD pattern having peaks at 5.7, 7.1, 11.3, 17.7 and 19.1 degrees 2-theta±0.2 degrees 2-theta, and also having one, two, three, four or five additional peaks selected from 16.5, 17.0, 20.7, 22.4 and 23.9 degrees 2-theta±0.2 degrees 2-theta.

* * * * *